United States Patent
Sikorski et al.

(10) Patent No.: US 6,569,905 B1
(45) Date of Patent: May 27, 2003

(54) COMBINATIONS OF CHOLESTERYL ESTER TRANSFER PROTEIN INHIBITORS AND BILE ACID SEQUESTERING AGENTS FOR CARDIOVASCULAR INDICATIONS

(75) Inventors: James A. Sikorski, Des Peres, MO (US); Kevin C. Glenn, Maryland Heights, MO (US)

(73) Assignee: G.D. Searle, LLC, Chicago, IL (US)

( * ) Notice: Subject to any disclaimer, the term of this patent is extended or adjusted under 35 U.S.C. 154(b) by 0 days.

(21) Appl. No.: 09/466,469

(22) Filed: Dec. 17, 1999

Related U.S. Application Data
(60) Provisional application No. 60/142,682, filed on Jul. 7, 1999, and provisional application No. 60/113,955, filed on Dec. 23, 1998.

(51) Int. Cl.$^7$ .......................... A61P 9/10; A61K 31/131; A61K 31/785; A61K 31/787
(52) U.S. Cl. ........................ 514/661; 514/672; 514/824; 424/78.18; 424/78.22; 424/78.35
(58) Field of Search .............................. 514/824, 425, 514/667, 672; 424/78.18, 78.22, 78.35

(56) References Cited

U.S. PATENT DOCUMENTS

| | | |
|---|---|---|
| 3,262,850 A | 7/1966 | Glynne |
| 3,287,370 A | 11/1966 | Mohrbacher |
| 3,389,144 A | 6/1968 | Mohrbacher |
| 3,520,891 A | 7/1970 | Mohrbacher |
| 3,674,836 A | 7/1972 | Creger |
| 3,692,895 A | 9/1972 | Nelson |
| 3,694,446 A | 9/1972 | Houlihan et al. |
| 3,714,190 A | 1/1973 | Boissier |
| 3,781,328 A | 12/1973 | Witte |
| 3,948,973 A | 4/1976 | Phillips |
| 3,962,261 A | 6/1976 | Zinnes |
| 3,972,878 A | 8/1976 | Schirmann |
| 3,983,140 A | 9/1976 | Endo |

(List continued on next page.)

FOREIGN PATENT DOCUMENTS

| | | |
|---|---|---|
| AU | A-30209/92 | 12/1992 |
| AU | A-61946/94 | 6/1994 |
| AU | A-61948/94 | 6/1994 |
| AU | A-61949/94 | 6/1994 |
| CA | 2025294 | 3/1991 |
| CA | 2078588 | 3/1993 |
| CA | 2085782 | 6/1993 |
| CA | 2085830 | 6/1993 |
| DE | 1211258 | 2/1968 |
| DE | 3 122 499 A1 | 12/1981 |
| DE | 196 27 430 A1 | 8/1996 |
| EP | 0 022 487 A1 | 1/1981 |
| EP | 0 033 538 B1 | 8/1981 |
| EP | 0 067 086 | 10/1982 |
| EP | 0 129 748 | 2/1985 |

(List continued on next page.)

OTHER PUBLICATIONS

A. Barrett et al., "Total Synthesis and Stereochemical Assignment of the Quinquecyclopropane–Containing Cholesteryl Ester Transfer Protein Inhibitor U–106305", J. Am Chem. Soc., 1996, 118, pp. 7863–7864.

P. Barter et al. "High Density Lipoproteins and Coronary Heart Disease", Atherosclerosis, 121 1996, pp. 1–12.

A. Beckwith et al., "Iododediazoniation of Arenediazonium Salts Accompanied by Aryl Radical Ring Closure", J. Org. Chem. 1987, vol. 52, pp. 1922–1930.

D. Bilheimer et al., "Mevinolin and Colestipol Stimulate Receptor–Mediated Clearance of Low Density Lipoprotein From Plasma In Familial Hypercholesterolemia Heterzygotes", Proc. Natl. Acad. Sci. USA, vol. 80, Jul. 1983, pp. 4124–4128.

C. Bisgaier et al., Cholesteryl Ester Transfer Protein Inhibition By PD 140195, Lipids, vol. 29, No. 12, 1994, pp. 811–818.

D. Blankenhorn et al., "Beneficial Effects of Combined Colestipol–Niacin Therapy On Coronary Atherosclerosis and Coronary Venous Bypass Grafts", JAMA, Jun. 19, 1987, vol. 257, No. 23, pp. 3233–3240.

D. Blankenhorn et al., "Beneficial Effects of Colestipol–Niacin Therapy on the Common Carotid Artery" Circulation vol. 88, Jul. 1, 1993, pp. 20–28.

P. Bonin et al., "A Peptide Inhibitor Of Cholesteryl Ester Transfer Protein Identified By Screening a Bacteriophage Display Library", Journal of Peptide Research, 51, 1998, pp. 216–225.

G. Brown, et al., "Regression of Coronary Artery Disease As A Result of Intensive Lipid–Lowering Therapy in Men With High Levels Of Apolipoprotein B", The New England Journal of Medicine, vol. 323, Nov. 8, 1990, No. 19, pp. 1289–1339.

M. Brown et al., Induction of 3–hydroxy–3Methylglutaryl Coenzyme A Reductase Activity in Human Fibroblasts Incubated with Compactin (ML–236B), A Competitive Inhibitor of the Reductase, The Journal of Biological Chemistry, vol. 253, No. 4, Feb. 22, 1978, pp. 1121–1128.

S. Busch et al., "Cholesteryl Ester Analogs Inhibit Cholesteryl Ester But Not Triglyceride Transfer Catalyzed By The Plasma Cholesteryl Ester–Triglyceride Transfer Protein", Lipids, vol. 25, No. 4 (1990), pp. 216–220.

C. Camoutsis et al., "N–Substituted 4, 5–Dihydro–1, 2–Benzothiazepin–3–One 1, 1–Dioxide", J. Heterocyclic Chem. 17, pp. 1135–1136 (1980).

(List continued on next page.)

Primary Examiner—Edward J. Webman
(74) Attorney, Agent, or Firm—Banner & Witcoff, Ltd.

(57) ABSTRACT

The present invention provides combinations of cardiovascular therapeutic compounds for the prophylaxis or treatment of cardiovascular disease including hypercholesterolemia and atherosclerosis. Combinations disclosed include an cholesteryl ester transfer protein inhibitor combined with a bile acid sequestrant.

10 Claims, No Drawings

U.S. PATENT DOCUMENTS

| | | | |
|---|---|---|---|
| 4,002,750 | A | 1/1977 | Ambrogi |
| 4,058,552 | A | 11/1977 | Mieville |
| 4,185,109 | A | 1/1980 | Rosen |
| 4,231,938 | A | 11/1980 | Monaghan |
| 4,251,526 | A | 2/1981 | McCall |
| 4,346,227 | A | 8/1982 | Terahara |
| 4,410,629 | A | 10/1983 | Terahara et al. |
| 4,444,784 | A | 4/1984 | Hoffman |
| 4,448,979 | A | 5/1984 | Terahara et al. |
| 4,559,332 | A | 12/1985 | Grob |
| 5,075,293 | A | 12/1991 | Reifschneider |
| 5,153,184 | A | 10/1992 | Reifschneider |
| 5,158,943 | A | 10/1992 | Sohda |
| 5,244,887 | A | 9/1993 | Straub |
| 5,260,316 | A | 11/1993 | Van Duzer |
| 5,334,600 | A | 8/1994 | Van Duzer |
| 5,350,761 | A | 9/1994 | Van Duzer |
| 5,354,772 | A | 10/1994 | Kathawala |
| 5,430,116 | A | 7/1995 | Kramer |
| 5,502,045 | A | 3/1996 | Miettinen |
| 5,512,558 | A | 4/1996 | Enhsen |
| 5,519,001 | A | 5/1996 | Rampratap |
| 5,602,152 | A | 2/1997 | Berthelon |
| 5,610,151 | A | 3/1997 | Glombik |
| 5,663,165 | A | 9/1997 | Brieaddy |
| 5,703,188 | A | 12/1997 | Mandeville |
| 5,705,524 | A | 1/1998 | McGee |
| 5,723,458 | A | 3/1998 | Brieaddy |
| 5,767,115 | A | 6/1998 | Rosenblum |
| 5,929,062 | A | 7/1999 | Haines |
| 5,994,391 | A | 11/1999 | Lee |
| 6,020,330 | A | 2/2000 | Enhsen |
| 6,034,118 | A | 3/2000 | Bischofberger |

FOREIGN PATENT DOCUMENTS

| | | |
|---|---|---|
| EP | 0 250 265 | 6/1987 |
| EP | 0 244 364 A2 | 11/1987 |
| EP | 0 338 331 | 6/1989 |
| EP | 0 379 161 | 1/1990 |
| EP | 0 409 281 A1 | 1/1991 |
| EP | 0 531 901 A2 | 2/1992 |
| EP | 0 508 425 A1 | 9/1992 |
| EP | 0 549 967 A1 | 12/1992 |
| EP | 0 526 402 A1 | 2/1993 |
| EP | 0 559 064 A2 | 2/1993 |
| EP | 0 563 731 A1 | 3/1993 |
| EP | 0 568 898 A1 | 4/1993 |
| EP | 0 818 197 A1 | 6/1997 |
| EP | 0 818 448 A1 | 6/1997 |
| EP | 0 796 846 A1 | 7/1997 |
| EP | 0 801 060 A1 | 10/1997 |
| FR | 2 661 676 A1 | 2/1990 |
| GB | 1 211 258 | 11/1970 |
| GB | 2 077 264 A | 12/1981 |
| GB | 2 305 665 | 4/1997 |
| GB | 2 329 334 | 3/1999 |
| JP | 10-287662 | 10/1998 |
| WO | 95/21843 | 8/1975 |
| WO | 89/01477 | 2/1989 |
| WO | 91/08205 | 6/1991 |
| WO | 92/17467 | 10/1992 |
| WO | 92/18115 | 10/1992 |
| WO | 92/18462 | 10/1992 |
| WO | 93/16055 | 8/1993 |
| WO | 93/21146 | 10/1993 |
| WO | 94/18183 | 8/1994 |
| WO | 94/18184 | 8/1994 |
| WO | 94/24087 | 10/1994 |
| WO | 96/05188 | 2/1996 |
| WO | 96/08484 | 3/1996 |
| WO | 96/16051 | 5/1996 |
| WO | 96/40255 | 12/1996 |
| WO | 97/03953 | 2/1997 |
| WO | 97/33882 | 9/1997 |
| WO | 97/49387 | 12/1997 |
| WO | 97/49736 | 12/1997 |
| WO | 98/02432 | 1/1998 |
| WO | 98/06405 | 2/1998 |
| WO | 98/23593 | 6/1998 |
| WO | 98/35937 | 8/1998 |
| WO | WO 98/38182 | 9/1998 |
| WO | 98/38182 | 9/1998 |
| WO | 98/39299 | 9/1998 |
| WO | WO 98/40375 | 9/1998 |
| WO | 98/40375 | 9/1998 |
| WO | 98/56757 | 12/1998 |
| WO | 99/11259 | 3/1999 |
| WO | 99/11260 | 3/1999 |
| WO | 99/11263 | 3/1999 |
| WO | 99/14174 | 3/1999 |
| WO | 99/14204 | 3/1999 |
| WO | 99/14215 | 3/1999 |
| WO | 99/32478 | 7/1999 |
| WO | 99/35135 | 7/1999 |
| WO | 99/64409 | 12/1999 |
| WO | 00/35889 | 6/2000 |

OTHER PUBLICATIONS

L. Cashin–Hemphill et al., "Beneficial Effects of Colestipol–Niacin on Coronary Atherosclerosis A 4–Year Follow–up", JAMA, Dec. 19, 1990, vol. 264, No. 23, pp. 3013–3017.

P. Catsoulacos et al., "Synthesis of Some N–Substituted 4,5–Dihydro–7,8–dimethoxybenzothiazepin–3–one 1,1–Dioxides", J. Heterocyclic Chem., vol. 13 (1976), pp. 1309–1314.

P. Catsoulacos et al., "Thiazo Compounds Derivatives of 4, 5–Dihydro–7, 8–Dimethoxybenzothiazepin–3 one 1, 1–Dioxides", Journal of Chemical and Engineering Data, vol. 22, No. 3, 1977, pp. 353–354.

K. Cho et al, "A Peptide From Hog Plasma that Inhibits Human Cholesteryl Ester Transfer Protein", Biochimica et Biophysica Acta, 1391, 1998, pp. 133–144.

D. Connolly et al., "Inactivation of Cholesteryl Ester Transfer Protein by Cysteine Modification", Biochemical and Biophysical Research Communications 223, pp. 42–47, 1996.

S. Coval et al., "Wiedendiol–A and–B, Cholesteryl Ester Transfer Protein Inhibitors From The Marine Sponge Xestosponga Wiedenmayeri", Bioorganic & Medicinal Chemistry Letter, vol. 5, No. 6, pp. 605–610, 1995.

J. Davignon et al., "Apolipoprotiein E and Atherosclerosis: Quest for an APO E Receptor Defect Leads to the Discovery of Pseudo Type III Dyslipoproteinemia in a Family", Atherosclerosis IX, pp. 199–203.

J. Davignon et al., "Comparative Efficacy and Safety of Pravastatin, Nicotinic Acid and The Two Combined in Patients with Hypercholesterolemia", The American Journal of Cardiology, Feb. 15. 1994, pp. 339–345.

C. East et al., "Combination Drug Therapy for Familial Combined Hyperlipidemia", Annals of Internal Medicine, Jul. 1, 1988, pp. 25–32.

J. Emmerich et al., "Efficacy and Safety of Simvastatin (Alone or in Association with Cholestyramine) A 1 yr. Study in 66 Patients with Type II Hyperlipoproteinaemai", European Heart Journal (1990), 11, pp. 149–155.

D. Erkelens, "Combination Drug Therapy with HMG Co A Reductase Inhibitors and Bile Acid Sequestrants for Hypercholesterolmia", Cardiology, 1990, 77, (suppl 4), pp. 33–38.

H. Ginsberg, "Update on the Treatment of Hypercholesterolemia, with a Focus on HMG–CoA Reductase Inhibitors and Combination Regimens", Clinical Cardiology 18, pp. 307–315, (1995).

C. Glueck et al., "Gemfibrozil–Lovastatin Therapy for Primary Hyperlipoproteinemias" The American Journal of Cardiology, Jul. 1, 1992, vol. 70, No. 1, pp. 1–9.

S. Grundy et al., "Influence of Combined Therapy with Mevinolin and Interruption of Bile–Acid Reabsorption on Low Density Lipoproteins in Heterozygous Familial Hypercholesterolemia", Annals of Internal Medicine, 1985, 103: pp. 339–343.

H. Gylling et al., "Effects Of Inhibiting Cholesterol Absorption And Synthesis On Cholesterol And Lipoprotein Metabolism In Hypercholesterolemic Non–Insulin–Dependent Diabetic Men", Journal of Lipid Research, vol. 37, 1996, pp. 1776–1785.

E. Haber, "Molecular Cardiovascular Medicine" Scientific American, pp. 35–40.

V. Hegde et al., "A Depsipeptide Fungal Metabolite Inhibitor Of Cholesteryl Ester Transfer Protein", Bioorganic & Medicinal Chemistry Letters 8, 1998, pp. 1277–1280.

L.Hellberg et al., "5a–Hydroxy–3a–Cholestanecarboxylic" The New Journal for Organic Synthesis, vol. 15, No. 1–2, Feb.–Apr. 1983, pp. 154–156.

J. Heubi et al., "Primary Bile Acid Malabsorption: Defective In Vitro Ileal Active Bile Acid Transport", Gastroenterolgy 1982, 83: pp. 804–811.

N. Hoogerbrugge et al., "The Additional Effects of Acipimox To Simvastatin In The Treatment of Combined Hyperlipidaemia", Journal of Internal Medicine, 1997, 241: pp. 151–155.

N. Hoogerbrugge et al., "The Effacy and Safety of Pravastatin, Compared To And In Combination With Bile Acid Binding Resins, In Familial Hypercholesterolaemia", Journal of Internal Medicine 1990, 228; pp. 261–266.

A. Hutchesson et al., "Dual Bezafibrate–Simvastatin Therapy For Combined Hyperlipidaemia", Journal of Clinical Pharmacy and Therapeutics 1994, 19, pp. 387–389.

T. Ichihashi, "Mechanism of Hypocholesterolemic Action of S–8921 in Rats: S–8921 Inhibits Ileal Bile Acid Absorption", The Journal Of Pharmacology And Experimental Therapeutics, vol. 284, No. 1, pp. 43–50.

D. Illingworth, et al., "Influence of Lovstatin plus Gemfibrozil on Plasma Lipids and Lipoproteins in Patients With Heterozygous Familial Hypercholesterolemia", Circulation vol. 79, No. 3, Mar. 1989, 590–596.

D. Illingworth, "Mevinolin Plus Colestipol in Therapy for Severe Heterozygous Familial Hypercholesterolemia", Annalos of Internal Medicine, 1984; 101, pp. 598–604.

Internal Search Report mailed May 23, 2000 based on PCT/US 99/27942.

International Search Report mailed May 23, 2000 based on PCT/US 99/27943.

Internal Search Report mailed May 23, 2000 based on PCT/US 99/27944.

International Search Report mailed May 23, 2000 based on PCT/US 99/277945.

International Search Report mailed May 18, 2000 based on PCT/US 99/27947.

International Search Report mailed May 15, 2000 based on PCT/US 99/27948.

International Search Report mailed May 17, 2000 based on PCT/US 99/27949.

J. Kane, et al., "Regression of Coronary Atherosclerosis During Treatment of Familial Hypercholesterolemia With Combined Drug Regimens", JAMA, Dec. 19, 1990, Chapter 26, vol. 264, No. 23, pp. 3007–3012.

A. Katritzky et al., "Preparation Of 6–7–And 8–Membered Sultams By Friedel–Crafts Cyclization Of w–Phenylalkanesulfamoyl Chlorides", Organic Preparations and Procedures Int., 24 (4), pp. 463–467 (1992).

T. Kazumi et al., "Effects of Niceritrol Of Elevated Serum Lipoprotein LP (A) Levels in Diabetic Patients With Or Without Overt Proteinuria", Current Therapeutic Research, vol. 55, No. 5, May 1994, pp. 546–551.

W. Kramer, et al., "Intestinal Bile Acid Absorption", The Journal of Biological Chemistry. vol. 268, No. 24 Issue of Aug. 25, pp. 18035–18046, 1993.

Kuo, M.S. et al., "Discovery, Isolation, Structure Elucidation, and Biosynthesis of U–106305, a Choresteryl Ester Transfer Protein Inhibitor from UC 11136", J. Am. Chem. Soc. 117, pp. 10629–10634 (1995).

Kvis, K. et al., "Benzocycloheptenes and Heterocyclic Analogues as Potential Drugs. VII, 4–Phenyl–,3,4,5–Tetrahydro–1–Benzothiepins and Some Related Compounds", Chem. Commun./Vo.37/(1973) pp. 3808–3816.

Lee, J.C. et al., "A Cholesteryl Ester Transfer Protein Inhibitor from an Insect–associated Fungus", The Journal of Antibiotics 49(7), pp. 693–696.

A.M. Lees et al., "Therapy of Hypercholesterolemia With Mevinolin And Other Lipid–Lowering Drugs", Arteriosclerosis 6, 1986, p. 544a.

T. Leren et al., "Effects of Lovastatin Alone and In Combination with Cholestyramine on Serum Lipids and Apolipoproteins in Heterozygotes for Familial Hypercholesterolemia", International Journal for Research and Investigation on Atherosclerosis and Related Diseases, 73, (1988), pp. 135–141.

M. Lewis, et al., Effects Of 2164U90 on Ileal Bile Acid Absorption and Serum Cholesterol in Rats and Mice, Journal of Lipid Research, vol. 36, 1995,pp. 1098–1105.

R. Lewis, Hawley's Condensed Chemical Dictionary, p. 1238.

W. Ling et al., "Minireview Dietary Phytosterols A Review of Metabolism, Benefits and Side Effects", Life Sciences, vol. 57, No. 3, 1995, pp. 195–206.

H. Mabuchi et al., "Reduction of Serum Cholesterol In Heterozygous Patients with Familial Hypercholesterolemia", The New England Journal of Medicine, vol. 308, Mar. 17, 1983, pp. 609–613.

M. Malloy et al., "Complementarity of Colestipol, Niacin, and Lovastatin in Treatment of Severe Familial Hypercholesterolemia", Annals of Internal Medicine 1987; 107: pp. 616–623.

W. Mandeville et al., Bile Acid Sequestrants: Their Use In Combination With Other Lipid–Lowering Agents, Idrugs 1999 vol. 2., No. 3, pp. 237–242.

G. Marais et al., "Rhabdomyolysis and Acute Renal Failure Induced by Combination Lovastatin and Gemfibrozil Therapy", Annals of Internal Medicine, Feb. 1, 1990, vol. 112, No. 3, pp. 228–230.

P. McCarthy, "New Approaches to Atherosclerosis: An Overview", Medicinal Research Reviews, vol. 13, No. 2, 1993, pp. 139–159.

R. Morton, Regulation of Lipid Transfer Between Lipoproteins By An Endogenous Plasma Protein: Selective Inhibition Among Lipoprotein Classes, Journal of Lipid Research, vol. 35, 1994, pp. 836–847.

F. Nerdel et al., "Quartermay Salts of B–Amino Aldehydes and B–Iodoaldehydes", Chemische Berichte (Ed. H. Zahn), vol. 98 (1965), pp. 728–734.

M. Newman et al., "The Conversion of Phenols to Thiophenols via Dialkylthiocarbamates", The Journal Or Organic Chemistry, vol. 31, Sep.–Dec. 1966, pp. 3980–3984.

A. Orahovats et al., "A Ring Enlargement from Seven–To Ten–Membered–Ring Sulfonamide Derivatives", Helvetica Chimica Acta, vol. 79, (1996), pp. 1121–1128.

H. Pan et al., "Pharmacokinetics and Pharmacodynamics of Pravastatin Alone and With Cholestyramine in Hypercholesterolemia", Clin. Pharmacol Ther. (1980) 9, 313, pp. 201–207.

N. Panagiotopoulos et al., "N(P–Bromophenyl)—4,5—Dihydro—7,8—Dimethoxy Benzothiazepine—ONE 1, 1–Dioxide C17 H16 brNO5S", Cryst. Struct. Comm. (1980) 9, pp. 313–319.

R. Pasternak et al., "Effect of Combination Therapy with Lipid–Reducing Drugs in Patients with Coronary Heart Disease and "Normal" Cholesterol Levels", Annals of Internal Medicine, Oct. 1, 1996, vol. 125, No. 7, pp. 529–538.

R. Patra et al., "Conformational and Steric Requirements Of The Side Chain For Sulphur Participation In Benzthiepin Derivatives", Tetrahedron Letters, vol. 30, No. 32, pp. 4279–4282, 1989.

R. Pierce et al., Myopathy and Rbabdomyolysis Associated With Lovastatin–Gemfibrozil Combination Therapy, JAMA, Jul. 4, 1990, vol. 264, No. 1, pp. 71–75.

W. Pirkle et al., "Trichlorosilane–Induced Cleavage. A Mild Method for Retrieving Carbinols From Carbamates", Jouranal Organic Chemistry, vol. 42, No. 15, 1977, pp. 2781–2782.

W. Pirkle et al., "Dynamic NMR Studies of Disatereomeric Carbamates: Implications toward the Determination of Relative Configuration by NMR" Journal of Organic Chemistry, vol. 44, No. 26, 1979, pp. 4891–4896.

W. Pirkle et al., "An Example of Automated Liquid Chromatography Synthesis of a Broad–Spectrum Resolving Agent and Resolution of 1–(Naphthyl) 2,2,2–Trifluoroethanol", The Journal of Organic Chemistry vol. 39, No. 26, 1974, pp. 3904–3906.

T. Pietzonka et al., "Phosphonate–Containing Analogs Of Cholesteryl Ester As Novel Inhibitors Of Cholesteryl Ester Transfer Protein", Bioorganic & Medicinal Chemistry Letters, vol. 6, No. 16, pp. 1951–1954.

Pravastatin Multicenter Study Group II, "Comparative Efficacy and Safety of Pravastatin and Cholestyramine Alone And Combined in Patients With Hypercholesterolemia", Archives of Internal Medicine, vol. 153, Jun. 14, 1993, pp. 1321–1328.

E. Reihner et al., Regulation of Hepatic Cholesterol Metabolism In Humans: Stimulatory Effects of Cholestyramine on HMG–CoA Reductase Activity and Low Density Lipoprotein Receptor Expression In Gallstone Patients, Journal of Lipid Research, vol. 31, 1990, pp. 2219–2226.

R. Remick et al., "Comparison of Fluoxetine and Desipramine In Depressed Outpatients", Therapeutic Research, vol. 53, No. 5, May 1993, pp. 457–483.

S. Rosenblum et al., Discovery of 1–(4–Fluorophenyl)–(3R)– [3–(4–fluorophenyl)–(3S)–hydroxypropyl]– (4S)–(4–hydroxyphenyl)–2–azetidinone (SCH 58235): A Designed, Potent, Orally hydroxypropyl]– (4S)–(4–hydroxyphenyl)–2–azetidinone (SCH 58255): A Designed, Potent, Orally Active Inhibitor of Cholesterol Absorption, Journal of Medicinal Chemistry, 1998, vol. 41, No. 6, pp. 973–980.

G. Salem et al., "Benzothiazine and Benzothizepine Derivatives: Structures of N–p–Bromophenyl–6, 7–Dimethoxy–1, 2–Benzothiazin–3(4H)–One 1, 1–Dioxide (BBTZ) and 4, 5–Dihydro–8,9–Dimethoxy–N–(5–Methyl–2–Pyridyl)–1, 2–Benzothiazepin–3–One 1, 1–Dioxide (MPTE)", Acta Cryst. (1986) C42, pp. 1581–1584.

J. Sasaki et al., "Effects of Fluvastatin, A New Inhibitor of HMG–CoA Reductase, and Niceritol on Serum Lipids, Lipoproteins and Cholesterol Ester Transfer Activity In Primary Hypercholesterolemic Patients", International Journal of Clinical Pharmacology and Therapeutics, vol. 33, No. 7, 1995, pp. 420–426.

K. Sindelar et al., Neurotropic and Psychotropic Compounds. XXIX. Derivatives Of 2,3,4, 5–Tetrahydro–1–Benzothiepin, Chemical Commun., vol. 33, 1968, pp. 4315–4327.

K. Sindelar et al., Benzocycloheptenes and Hete 1 rocyclic Analogues As Potential Drugs III. Further Synthetic Experiments In The Series Of 1–Benzothiepin Derivatives, vol. 37, 1972, 1195–1206.

C. Sirtori, "New Targets For Lipid Lowering And Atherosclerosis Prevention", Pharmac. Ther. vol. 67, No. 3., pp. 433–447, 1995.

Y. Son, "Purification and Characterization of Human Plasma Proteins That Inhibit Lipid Transfer Activities", Biochimica et Biophysica Acta, 795, 1984, pp. 473–480.

D. Sprecher et al., "Low–Dose Combined Therapy with Fluvastin and Cholestyramine in Hyperlipidemic Patients", Ann Intern Med. 1994; 120: pp. 537–543.

C.I. Stassinopoulou, et al., "C NMR Spectra of Benzothiazepinone, Benzothiazinone and Benzosulphonamide N–Substituted Derivatives" Department of Biology, Nuclear Research Center.

E. Stedronsky et al., "Interaction of Bile Acids and Cholesterol with Non–Systemic Agents Having Hypocholesterolemic Properties", Biochimica et Biophysica Acta., 1210, 1994, pp. 255–287.

I. Stein, et al., "Effects of Simvastatin and Cholestyramine in Familial and Nonfamilial Hypercholesterolemia", Arch Intern Med. vol. 150, Feb. 1990, pp. 341–345.

E. Stein, et al., "Lovastatin Alone And In Combination For Treatment Of Primary Hypercholesterolema", Alan R. Liss, Inc. 1988, pp. 281–293.

K. Suckling, et al., Cholesterol Lowering and Bile Acid Excretion in the Hamster with Cholestyramine Treatment, Atherosclerosis, 89, (1991) pp. 183–190.

T. Swenson, "Mechanism of Cholesteryl Ester Transfer Protein Inhibition by a Neutralizing Monoclonal Antibody and Mapping of the Monoclonal Antibody Epitope", The Journal of Biological Chemistry, vol. 264, No. 24, Aug. 25, pp. 14318–14326, 1989.

A. Tall, "Plasma Cholesteryl Ester Transfer Protein", Journal of Lipid Research, vol. 34, 1993, pp. 1255–1274.

Y. Tamura et al., Novel Conversions of Benzo [b] thiophen–3 (2–H)–ones into 1,2–Benzisothiazole and Tetrahydro–1,2–Benzothiazepin–5–One Systems via Sulphimide Intermediates, J.C.S. Perkin I, pp. 2830–2834.

K. Thurmond et al., "Water–Soluble Knedel–like Structures: The Preparation of Shell–Cross–Linked Small Particles", Journal American Chemistry Soc. vol., 118, No. 30, 1996, pp. 7239–7240.

P. Tyle, "Iontophoretic Devices for Drug Delivery", Pharmaceutical Research, vol. 3, No. 6, 1986, pp. 318–325.

M. Une et al., Metabolism of 3a, 7a–Dihydroxy–7b–Methyl–5b–Cholanoic Acid and 3a, 7B–Dihydroxy–7a–Methyl–5B–Cholanoic Acid Hamsters, Biochimica et Biophysica Acta, 833 (1985), pp. 196–202.

J. Vacek et al., Comparison of Lavastatin (20 mg) and Nicotinic Acid (1.2g) With Either Drug Alone for Type II Hyperlipoproteinemia, The American Journal Of Cardiology, vol. 76, Jul. 15, 1995, pp. 182–184.

M. Van Heek et al., "In Vivo Metabolism–Based Discovery of a Potent Cholesterol Absorption Inhibitor, SCH58235, in the Rat and Rhesus Monkey Through the Identification of the Active Metabolites of SCH48461", The Journal of Pharmacology and Experimental Therapeutics, vol. 283, No. 1, pp. 157–754.

G. Vega et al., "Treatment of Primary Moderate Hypercholesterolemia With Lovastatin (Mevinolin) and Colestipol", JAMA, Jan. 2, 1987, vol. 257, No. 1, pp. 33–37.

G. Wess et al., "Synthesis and Biological Activity of Bile Acid–Derived HMG–CoA Reductase Inhibitors. The Role of 21–Methyl in Recognition of HMG–CoA Reductase and the Ileal Bile Acid Transport System", Journal Of Medicinal Chemistry 1994, 37, pp. 3240–3246.

J. Wetterau et al., "An MTP Inhibitor that Normalizes Atherogenic Lipoprotein Levels In WHHL Rabbits", Science vol. 282, Oct. 23, 1998, pp. 751–754.

O. Wiklund et al., "Pravastatin and Gemfibrozil Alone and in Combination for the Treatment of Hypercholesterolemia", The American Journal of Medicine vol. 94, Jan. 1993, pp. 13–19.

S. Wirebaugh et al., "A Retrospective Review of the Use of Lipid–Lowering Agents in Combination, Specifically, Gemfibrozil and Lovastatin", Pharmacotherapy vol. 12, No. 6, 1992, pp. 445–450.

J. Witztum, "Drugs Used In The Treatment of Hyperlipoproteinemias", The Pharmacological Basis of Therapeutics, $9^{th}$ Edition, pp. 875–894.

Yan Xia et al., "Substituted 1,3,5–Triazines As Cholesteral Ester Transfer Protein Inhibitors", Bioorganic & Medicinal Chemistry Letters, vol. 6, No. 7, 1996, pp. 919–922.

A. Yamamoto et al., "Effects of Probucol on Xanthomata Regression in Familial Hypercholesterolemia", Am Journal Cardiolgy, 1986, 57: pp. 29H–35H.

K. Ytre–Arne et al., "Simvastatin and Cholestyramine In The Long–Term Treatment of Hypercholesterolaemia", Journal of Internal Medicine (1989): 226, pp. 285–290.

Angelin, B., "Regulation of Hepatic Cholesterol Metabolism In Man," Ann. Med. 23, pp. 10–27 (1991).

Blum, C. B., "Comparison of Properties of Four Inhibitors of 3–Hydroxy–3–Methylglutaryl–Coenzyme A Reductase," Am. J. Cardiol., 73(14), 3D–11D, (1994).

Cayen, M.N., "Disposition, Metabolism and Pharmacokinetics of Anthyperlipidemic Agents in Laboratory Animals and Man," Pharmac & Ther., 29, pp. 157–204 (1985).

Da Col, et al., "Tolerability and Efficacy of Combination Therapy with Simvastatin Plus Gemfibroail in Type II Refractory Familial Combined Hyperllpidemia," Curr. Therap. Research, vol. 53, No. 5, pp. 473–483 (1993).

Davignon, et al., "HMG CoA Reductase Inhibitors: A look back and a look ahead," Can. J. Cardiol., 8(8), pp. 843–864 (1992).

Endo, A. "Chemistry, biochemistry and pharmacology of HMG–Co–A reductase inhibitors," Klin. Wochemschr. 66, pp. 421–427 (1988).

Kramer et al., "Bile acid derived HMG–CoA reductase inhibitors," Biochemica dt Biophysica Acta, 1227 pp. 137–154 (1994).

Marcus, A., "Role of the HMG–CoA Reductase Inhibitors in the Treatment of Dyslipidemla: An Evolutionary Review," CVR&R, pp. 13–27 (Jan. 1996).

US 6,569,905 B1

COMBINATIONS OF CHOLESTERYL ESTER TRANSFER PROTEIN INHIBITORS AND BILE ACID SEQUESTERING AGENTS FOR CARDIOVASCULAR INDICATIONS

This application claims priority of U.S. provisional application Ser. No. 60/142,682 filed Jul. 7, 1999 and of U.S. provisional application Ser. No. 60/113,955 filed Dec. 23, 1998.

BACKGROUND OF THE INVENTION

1. Field of the Invention

The present invention relates to methods of treating cardiovascular diseases, and specifically relates to combinations of compounds, compositions, and methods for their use in medicine, particularly in the prophylaxis and treatment of hyperlipidemic conditions such as are associated with atherosclerosis, hypercholesterolemia, and other coronary artery disease in mammals. More particularly, the invention relates to cholesteryl ester transfer protein (CETP) activity inhibiting compounds. The invention also relates to bile acid sequestering compounds.

2. Description of Related Art

It is well-settled that hyperlipidemic conditions associated with elevated concentrations of total cholesterol and low-density lipoprotein (LDL) cholesterol are major risk factors for coronary heart disease and particularly atherosclerosis. Numerous studies have demonstrated that a low plasma concentration of high density lipoprotein (HDL) cholesterol is a powerful risk factor for the development of atherosclerosis (Barter and Rye, *Atherosclerosis*, 121, 1–12 (1996). HDL is one of the major classes of lipoproteins that function in the transport of lipids through the blood. The major lipids found associated with HDL include cholesterol, cholesteryl ester, triglycerides, phospholipids and fatty acids. The other classes of lipoproteins found in the blood are low density lipoprotein (LDL), intermediate density lipoprotein (IDL), and very low density lipoprotein (VLDL). Since low levels of HDL cholesterol increase the risk of atherosclerosis, methods for elevating plasma HDL cholesterol would be therapeutically beneficial for the treatment of atherosclerosis and other diseases associated with accumulation of lipid in the blood vessels. These diseases include, but are not limited to, coronary heart disease, peripheral vascular disease, and stroke.

Atherosclerosis underlies most coronary artery disease (CAD), a major cause of morbidity and mortality in modern society. High LDL cholesterol (above about 180 mg/dl) and low HDL cholesterol (below 35 mg/dl) have been shown to be important contributors to the development of atherosclerosis. Other diseases or risk factors, such as peripheral vascular disease, stroke, and hypercholesterolaemia are negatively affected by adverse HDL/LDL ratios.

Interfering with the recirculation of bile acids from the lumen of the intestinal tract is found to reduce the levels of serum cholesterol in a causal relationship. Epidemiological data has accumulated which indicates such reduction leads to an improvement in the disease state of atherosclerosis. Stedronsky, in "Interaction of bile acids and cholesterol with nonsystemic agents having hypocholesterolemic properties," *Biochimica et Biophysica Acta*, 1210, 255–287 (1994) discusses the biochemistry, physiology and known active agents surrounding bile acids and cholesterol.

Inhibition of cholesteryl ester transfer protein (CETP) has been shown to effectively modify plasma HDL/LDL ratios, and is expected to check the progress and/or formation of certain cardiovascular diseases. CETP is a plasma protein that facilitates the movement of cholesteryl esters and triglycerides between the various lipoproteins in the blood (Tall, *J. Lipid Res.*, 34, 1255–74 (1993)). The movement of cholesteryl ester from HDL to LDL by CETP has the effect of lowering HDL cholesterol. It therefore follows that inhibition of CETP should lead to elevation of plasma HDL cholesterol and lowering of plasma LDL cholesterol, thereby providing a therapeutically beneficial plasma lipid profile. Evidence of this effect is described in McCarthy, *Medicinal Res. Revs.*, 13, 139–59 (1993). Further evidence of this effect is described in Sitori, *Pharmac. Ther.*, 67, 443–47 (1995)). This phenomenon was first demonstrated by Swenson et al., (*J. Biol. Chem.*, 264, 14318 (1989)) with the use of a monoclonal antibody that specifically inhibits CETP. In rabbits, the antibody caused an elevation of the plasma HDL cholesterol and a decrease in LDL cholesterol. Son et al. (*Biochim. Biophys. Acta*, 795, 743–480 (1984)) describe proteins from human plasma that inhibit CETP. U.S. Pat. No. 5,519,001, herein incorporated by reference, issued to Kushwaha et al., describes a 36 amino acid peptide derived from baboon apo C-1 that inhibits CETP activity. Cho et al. (*Biochim. Biophys. Acta* 1391, 133–144 (1998)) describe a peptide from hog plasma that inhibits human CETP. Bonin et al. (*J. Peptide Res.*, 51, 216–225 (1998)) disclose a decapeptide inhibitor of CETP. A depspeptide fungal metabolite is disclosed as a CETP inhibitor by Hedge et al. in *Bioorg. Med. Chem. Lett.*, 8, 1277–80 (1998).

There have been several reports of non-peptidic compounds that act as CETP inhibitors. Barrett et al. (*J. Am. Chem. Soc.*, 188, 7863–63 (1996)) describe cyclopropane-containing CETP inhibitors. Further cyclopropane-containing CETP inhibitors are described by Kuo et al. (*J. Am. Chem. Soc.*, 117, 10629–34 (1995)). Pietzonka et al. (*Bioorg. Med. Chem. Lett.*, 6, 1951–54 (1996)) describe phosphonate-containing analogs of cholesteryl ester as CETP inhibitors. Coval et al. (*Bioorg. Med. Chem. Lett.*, 5, 605–610 (1995)) describe Wiedendiol-A and -B, and related sesquiterpene compounds as CETP inhibitors. Lee et al. (*J. Antibiotics*, 49, 693–96 (1996)) describe CETP inhibitors derived from an insect. fungus. Busch et al. (*Lipids*, 25, 216–220, (1990)) describe cholesteryl acetyl bromide as a CETP inhibitor. Morton and Zilversmit (*J. Lipid Res.*, 35, 836–47 (1982)) describe that p-chloromercuriphenyl sulfonate, p-hydroxymercuribenzoate and ethyl mercurithiosalicylate inhibit CETP. Connolly et al. (*Biochem. Biophys. Res. Comm.*, 223, 42–47 (1996)) describe other cysteine modification reagents as CETP inhibitors. Xia et al. describe 1,3,5-triazines as CETP inhibitors (*Bioorg. Med. Chem. Lett.*, 6, 919–22 (1996)). Bisgaier et al. (*Lipids*, 29, 811–8 (1994)) describe 4-phenyl-5-tridecyl-4H-1,2,4-triazole-thiol as a CETP inhibitor. Additional triazole CETP inhibitors are described in U.S. patent application Ser. No. 09/153,360, herein incorporated by reference. Sikorski et al. disclosed further novel CETP inhibitors in PCT Patent Application No. WO 9914204.

Substituted 2-mercaptoaniline amide compounds can be used as CETP inhibitors and such therapeutic compounds are described by H. Shinkai et al. in PCT Patent Application No. WO 98/35937.

Some substituted heteroalkylamine compounds are known as CETP inhibitors. In European Patent Application No. 796846, Schmidt et al. describe 2-aryl-substituted pyridines as cholesterol ester transfer protein inhibitors useful as cardiovascular agents. One substituent at $C_3$ of the pyridine ring can be an hydroxyalkyl group. In European Patent Application No. 801060, Dow and Wright describe heterocyclic derivatives substituted with an aldehyde addition product of an alkylamine to afford 1-hydroxy-1-amines. These are reported to be β3-adrenergic receptor agonists useful for treating diabetes and other disorders. In Great Britain Patent Application No. 2305665, Fisher et al. disclose 3-agonist secondary amino alcohol substituted pyridine derivatives useful for treating several disorders including cholesterol levels and atherosclerotic diseases. In European Patent Application No. 818448 (herein incorporated by reference), Schmidt et al. describe tetrahydroquinoline derivatives as cholesterol ester transfer protein inhibitors. European Patent Application No. 818197, Schmek et al. describe pyridines with fused heterocycles as cholesterol ester transfer protein inhibitors. Brandes et al. in German Patent Application No. 19627430 describe bicyclic condensed pyridine derivatives as cholesterol ester transfer protein inhibitors. In PCT Patent Application No. WO 9839299, Muller-Gliemann et al. describe quinoline derivatives as cholesteryl ester transfer protein inhibitors.

Polycyclic compounds that are useful as CETP inhibitors are also disclosed by A. Oomura et al. in Japanese Patent No. 10287662. For example, therapeutic compounds having the structures C-1 and C-8 were prepared by culturing Penicillium spp.

Cycloalkylpyridines useful as CETP inhibitors are disclosed by Schmidt et al. in European Patent No. EP 818448. For example, the therapeutic compound having the structure C-9 is disclosed as being particularly effective as a CETP inhibitor.

Substituted tetrahydronaphthalene compounds useful as CETP inhibitors are described in PCT Patent Application No. WO 9914174. Specifically described in that disclosure as a useful CETP inhibitor is (8S)-3-cyclopentyl-1-(4-fluorophenyl)-2-[(S)-fluoro(4-trifluoromethylphenyl) methyl]-8-hydroxy-6-spirocclobutyl-5,6,7,8-tetrahydronaphthalene.

Some 4-heteroaryl-tetrahydroquinolines useful as CETP inhibitors are described in PCT Patent Application No. WO 9914215. For example, that disclosure describes 3-(4-trifluoromethylbenzoyl)-5,6,7,8-tetrahydroquinolin-5-one as a useful CETP inhibitor.

Some combination therapies for the treatment of cardiovascular disease have been described in the literature. Combinations of IBAT inhibitors with HMG CoA reductase inhibitors useful for the treatment of cardiovascular disease are disclosed in U.S. patent application Ser. No. 09/037,308.

A combination therapy of fluvastatin and niceritrol is described by J. Sasaki et al. (Id.). Those researchers conclude that the combination of fluvastatin with niceritrol "at a dose of 750 mg/day dose does not appear to augment or attenuate beneficial effects of fluvastatin."

L. Cashin-Hemphill et al. (J. Am. Med. Assoc., 264 (23), 3013–17 (1990)) describe beneficial effects of a combination therapy of colestipol and niacin on coronary atherosclerosis. The described effects include nonprogression and regression in native coronary artery lesions.

A class of materials which operates by another mechanism to lower LDL cholesterol comprises bile acid sequestering agents ("bile acid sequestrants" or "bile acid sequestering compounds"). Such agents are typically anion exchange polymers administered orally to a patient. As the agent passes through the gut, anions of bile acids are sequestered by the agent and excreted. Such sequestering has been speculated to prevent reabsorption by the gut, for example the ileum, causing the body to increase conversion of cholesterol into bile acids, and thereby decreasing serum cholesterol levels. One such bile acid sequestering agent is cholestyramine, a styrene-divinylbenzene copolymer containing quaternary ammonium cationic groups capable of binding bile acids. It is believed that cholestyramine binds the bile acids in the intestinal tract, thereby interfering with their normal enterohepatic circulation. This effect is described by Reihnér et al., in "Regulation of hepatic cholesterol metabolism in humans: stimulatory effects of cholestyramine on HMG-CoA reductase activity and low density lipoprotein receptor expression in gallstone patients", Journal of Lipid Research, 31, 2219–2226 (1990). Further description of this effect is found in Suckling et al. in "Cholesterol Lowering and bile acid excretion in the hamster with cholestyramine treatment", *Atherosclerosis*, 89, 183–90 (1991). This results in an increase in liver bile acid synthesis because of the liver using cholesterol as well as an upregulation of the liver LDL receptors which enhances clearance of cholesterol and decreases serum LDL cholesterol levels.

Another bile acid sequestering agent is colestipol, a copolymer of diethylenetriamine and 1-chloro-2,3-epoxypropane. Colestipol is described in U.S. Pat. No. 3,692,895. A frequent side effect of colestipol and of cholestyramine is gastric distress.

Additional bile acid sequestering agents are described in U.S. Pat. No. 5,703,188, assigned to Geltex Pharmaceuticals, Inc. For example, one such bile acid sequestering agent is 3-methacrylamidopropyltrimethylammonium chloride copolymerized with ethylene glycol dimethacrylate to yield a copolymer.

Further bile acid sequestering agents are described in PCT Patent Application No. WO 98/57652, assigned to Geltex Pharmaceuticals, Inc. The WO 98/57652 application describes polyallylamine polymers.

An example of a bile acid sequestering agent is CholestaGel, CAS Registry No. 182815–44–7. CholestaGel is N,N,N-trimethyl-6-(2-propenylamino)-1-hexanaminium chloride polymer with (chloromethyl)oxirane, 2-propen-1-amine and N-2-propenyl-1-decanamine hydrochloride.

Yet another class materials proposed as bile acid sequestering agents comprises particles comprising amphiphilic copolymers having a crosslinked shell domain and an interior core domain (Patent application no. PCT/US 97/11610). Structures and preparation of such crosslinked amphiphilic copolymers are described in PCT/US97/11345. Such particles have been given the common name of "knedels" (K. B. Thurmond et al., J. Am. Chem. Soc., 118 (30), 7239–40 (1996)).

Some combination therapies for the treatment of cardiovascular disease have been described in the literature. Combinations of IBAT inhibitors with HMG CoA reductase inhibitors useful for the treatment of cardiovascular disease are disclosed in U.S. patent application Ser. No. 09/037,308, herein incorporated by reference.

A combination therapy of fluvastatin and niceritrol is described by J. Sasaki et al. (Id.). Those researchers conclude that the combination of fluvastatin with niceritrol "at a dose of 750 mg/day dose does not appear to augment or attenuate beneficial effects of fluvastatin."

L. Cashin-Hemphill et al. (J. Am. Med. Assoc., 264 (23), 3013–17 (1990), herein incorporated by reference) describe beneficial effects of a combination therapy of colestipol and niacin on coronary atherosclerosis. The described effects include nonprogression and regression in native coronary artery lesions.

A combination therapy of acipimox and simvastatin shows beneficial HDL effects in patients having high triglyceride levels (N. Hoogerbrugge et al., J. Internal Med., 241, 151–55 (1997), herein incorporated by reference).

Sitostanol ester margarine and pravastatin combination therapy is described by H. Gylling et al. (J. Lipid Res., 37, 1776–85 (1996), herein incorporated by reference). That therapy is reported to simultaneously inhibit cholesterol absorption and lower LDL cholesterol significantly in non-insulin-dependent diabetic men.

Brown et al. (New Eng. J. Med., 323 (19), 1289–1339 (1990), herein incorporated by reference) describe a combination therapy of lovastatin and colestipol which reduces atherosclerotic lesion progression and increase lesion regression relative to lovastatin alone.

A combination therapy of an apoB secretion inhibitor with a CETP inhibitor was disclosed by Chang et al. in PCT Patent Application No. WO9823593, herein incorporated by reference.

Buch et al. (PCT Patent Application No. WO 9911263, herein incorporated by reference) describe a combination therapy comprising amlodipine and a statin compound for treating subjects suffering from angina pectoris, atherosclerosis, combined hypertension and hyperlipidemia, and to treat symptoms of cardiac arrest. Buch et al. describe in PCT Patent Application No. WO 9911259 a combination therapy comprising amlodipine and atorvastatin.

Scott et al. (PCT Patent Application No. WO 9911260) describe a combination therapy comprising atorvastatin and an antihypertensive agent.

Dettmar and Gibson (UK Patent Application No. GB 2329334 A) claim a therapeutic composition useful for reducing plasma low density lipoprotein and cholesterol levels, wherein the composition comprises an HMG CoA reductase inhibitor and a bile complexing agent.

The above references show continuing need to find safe, effective agents for the prophylaxis or treatment of cardiovascular diseases.

SUMMARY OF THE INVENTION

To address the continuing need to find safe and effective agents for the prophylaxis and treatment of cardiovascular diseases, combination therapies of cardiovascular drugs are now reported.

Among its several embodiments, the present invention provides a combination therapy comprising the use of a first amount of an CETP inhibitor and a second amount of another cardiovascular therapeutic useful in the prophylaxis or treatment of hyperlipidemia, atherosclerosis, or hypercholesterolemia, wherein said first and second amounts together comprise an anti-hyperlipidemic condition effective amount, an anti-atherosclerotic condition effective amount, or an anti-hypercholesterolemic condition effective amount of the compounds. For example one of the many embodiments of the present invention is a combination therapy comprising therapeutic dosages of an CETP inhibitor and a bile acid sequestering agent.

A further embodiment of the instant invention comprises the use of any of the cardiovascular combination therapies described herein for the prophylaxis or treatment of hypercholesterolemia, atherosclerosis, or hyperlipidemia. Therefore, in one embodiment the present invention provides a method for the prophylaxis or treatment of a hyperlipidemic condition comprising administering to a patient in need thereof a combination in unit dosage form wherein the combination comprises a first amount of an bile acid sequestering compound and a second amount of a CETP inhibiting compound wherein the first amount and the second amount together comprise an anti-hyperlipidemic condition effective amount of the compounds.

In another embodiment, the present invention provides a method for the prophylaxis or treatment of an atherosclerotic condition comprising administering to a patient in need thereof a combination in unit dosage form wherein the combination comprises a first amount of an bile acid sequestering compound and a second amount of a CETP inhibiting compound wherein the first amount and the second amount together comprise an anti-atherosclerotic condition effective amount of the compounds.

In still another embodiment, the present invention provides method for the prophylaxis or treatment of hypercholesterolemia comprising administering to a patient in need thereof a combination in unit dosage form wherein the combination comprises a first amount of an bile acid sequestering compound and a second amount of a CETP inhibiting compound wherein the first amount and the second amount together comprise an anti-hypercholesterolemic condition effective amount of the compounds.

Further scope of the applicability of the present invention will become apparent from the detailed description provided below. However, it should be understood that the following detailed description and examples, while indicating preferred embodiments of the invention, are given by way of illustration only since various changes and modifications within the spirit and scope of the invention will become apparent to those skilled in the art from this detailed description.

DETAILED DESCRIPTION OF THE PREFERRED EMBODIMENTS

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

The contents of each of the references cited herein, including the contents of the references cited within these primary references, are herein incorporated by reference in their entirety.

a. Definitions

The following definitions are provided in order to aid the reader in understanding the detailed description of the present invention:

"Combination therapy" means the administration of two or more therapeutic agents to treat a hyperlipidemic condition, for example atherosclerosis and hypercholesterolemia. Such administration encompasses co-administration of these therapeutic agents in a substantially simultaneous manner, such as in a single capsule having a fixed ratio of active ingredients or in multiple, separate capsules for each inhibitor agent. In addition, such administration also encompasses use of each type of therapeutic agent in a sequential manner. In either case, the treatment regimen will provide beneficial effects of the drug combination in treating the hyperlipidemic condition.

The phrase "therapeutically effective" is intended to qualify the combined amount of inhibitors in the combination therapy. This combined amount will achieve the goal of reducing or eliminating the hyperlipidemic condition.

"Therapeutic compound" means a compound useful in the prophylaxis or treatment of a hyperlipidemic condition, including atherosclerosis and hypercholesterolemia.

b. Combinations

The combinations of the present invention will have a number of uses. For example, through dosage adjustment and medical monitoring, the individual dosages of the therapeutic compounds used in the combinations of the present invention will be lower than are typical for dosages of the therapeutic compounds when used in monotherapy. The dosage lowering will provide advantages including reduction of side effects of the individual therapeutic compounds when compared to the monotherapy. In addition, fewer side effects of the combination therapy compared with the monotherapies will lead to greater patient compliance with therapy regimens.

Another use of the present invention will be in combinations having complementary effects or complementary modes of action. For example, bile acid sequestering agents control blood serum cholesterol levels by inhibiting the reabsorption of bile acids in the ileum. In contrast, CETP inhibitors inhibit the movement of cholesteryl esters and triglycerides between the various lipoproteins in the blood.

Compounds useful in the present invention encompass a wide range of therapeutic compounds. Some individual CETP inhibitor compounds useful in the present invention are separately described in the following individual patent applications, each of which is herein incorporated by reference.

R9. U.S. Patent Application Serial No. 60/101661.
R10. U.S. Patent Application Serial No. 60/101711.
R11. U.S. Patent Application Serial No. 60/101660.
R12. U.S. Patent Application Serial No. 60/101664.
R13. U.S. Patent Application Serial No. 60/101668.
R14. U.S. Patent Application Serial No. 60/101662.
R15. U.S. Patent Application Serial No. 60/101663.
R16. U.S. Patent Application Serial No. 60/101669.
R17. U.S. Patent Application Serial No. 60/101667.
R18. U.S. patent application Ser. No. 09/401,916.
R19. U.S. patent application Ser. No. 09/405,524.
R20. U.S. patent application Ser. No. 09/404,638.
R21. U.S. patent application Ser. No. 09/404,638.
R22. U.S. patent application Ser. No. 09/400,915.
R23. U.S. Pat. No. 5,932,587.
R24. U.S. Pat. No. 5,925,645.

CETP inhibitor compounds of particular interest in the present invention include those shown in Table 1, as well as the diastereomers, enantiomers, racemates, salts, and tautomers of the CETP inhibitors of Table 1.

TABLE 1

| Compound Number | Structure |
|---|---|
| C-1 | (structure) |
| C-2 | (structure) |
| C-3 | (structure) |
| C-4 | (structure) |
| C-5 | (structure) |

TABLE 1-continued

| Compound Number | Structure |
| --- | --- |
| C-6 | [structure: 4-(2-methylphenyl)-5-tridecyl-2H-1,2,4-triazole-3(4H)-thione] |
| C-7 | [structure: N-(2-hydroxy-2-(trifluoromethyl)propyl... substituted diphenyl ether with Cl, ethyl, and CF3/CF2 groups] |
| C-8 | [complex polycyclic natural product structure with OCH3, OH, methyl, and acetyl groups] |
| C-9 | [structure: tetrahydroquinoline with 4-fluorophenyl, 4-(trifluoromethyl)phenyl-CHF, cyclopentyl, methyl, and OH substituents] |
| C-10 | [structure: diphenyl ether aminoalcohol with OCF3 and OCF2CF2H groups] |
| C-11 | [structure: similar aminoalcohol with CF3 and OCF2CF2H groups] |
| C-12 | [structure: diphenyl ether aminoalcohol with Cl, ethyl, and OCF2CF2H groups] |
| C-13 | [structure: diphenyl ether aminoalcohol with ethyl and OCF2CF2H groups] |

TABLE 1-continued

| Compound Number | Structure |
|---|---|
| C-14 | (structure) |
| C-15 | (structure) |
| C-16 | (structure) |
| C-17 | (structure) |
| C-18 | (structure) |
| C-19 | (structure) |
| C-20 | (structure) |

Bile acid sequestrants useful in the combinations and methods of the present invention comprise a wide variety of structures and functionalities. Preferred bile acid sequestrants for the present invention are described in Table 2. The therapeutic compounds of Table 2 can be used in the present invention in a variety of forms, including acid form, salt form, racemates, enantiomers, zwitterions, and tautomers. The individual patent documents referenced in Table 2 are each herein incorporated by reference. Additional bile acid sequestrants useful herein are particles comprising amphiphilic copolymers having a crosslinked shell domain and an interior core domain (knedels, Patent application No. PCT/US 97/11610, herein incorporated by reference). Knedels of particular interest in the present invention comprise polystyrene-b-poly(acrylic acid) (PS-b-PAA) crosslinked with one or more polyamine. Especially preferred knedels comprise PS-b-PAA crosslinked with 1-(3-dimethylaminopropyl)-3-ethylcarbodiimide methiodide and triethylenetetramine ("knedel A") or 1,7-diaza-4,10-diazonium-4,4,10,10-tetramethylundecane diiodide ("knedel B").

TABLE 2

| Compound Number | Common Name | CAS Registry Number | Patent Document Reference |
|---|---|---|---|
| G-35 | cholestyramine | 11041-12-6 | |
| G-46 | colestipol | 50925-79-6 | U.S. Pat. No. 3,692,895 |
| S-1 | knedel A | | PCT/US97/11345 |
| S-2 | knedel B | | PCT/US97/11345 |
| S-3 | 3-methacrylamido-propyltrimethyl-ammonium chloride copolymerized with ethylene glycol dimethacrylate | | U.S. Pat. No. 5,703,188 |
| S-4 | CholestaGel | 152751-57-0 | WO 98/57652 |
| S-5 | OmegaGel | | WO 98/57652 |

The compounds (for example, CETP inhibiting compounds or bile acid sequestering compounds) useful in the present invention can have no asymmetric carbon atoms, or, alternatively, the useful compounds can have one or more asymmetric carbon atoms. When the useful compounds have one or more asymmetric carbon atoms, they therefore include racemates and stereoisomers, such as diastereomers and enantiomers, in both pure form and in admixture. Such stereoisomers can be prepared using conventional techniques, either by reacting enantiomeric starting materials, or by separating isomers of compounds of the present invention.

Isomers may include geometric isomers, for example cis-isomers or trans-isomers across a double bond. All such isomers are contemplated among the compounds useful in the present invention.

The compounds useful in the present invention also include tautomers.

The compounds useful in the present invention as discussed below include their salts, solvates and prodrugs.

Dosages, Formulations, and Routes of Administration

The compositions of the present invention can be administered for the prophylaxis and treatment of hyperlipidemic diseases or conditions by any means, preferably oral, that produce contact of these compounds with their site of action in the body, for example in the ileum, plasma, or liver of a mammal, e.g., a human.

For the prophylaxis or treatment of the conditions referred to above, the compounds useful in the compositions and methods of the present invention can be used as the compound per se. Pharmaceutically acceptable salts are particularly suitable for medical applications because of their greater aqueous solubility relative to the parent compound. Such salts must clearly have a pharmaceutically acceptable anion or cation. Suitable pharmaceutically acceptable acid addition salts of the compounds of the present invention when possible include those derived from inorganic acids, such as hydrochloric, hydrobromic, phosphoric, metaphosphoric, nitric, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, succinic, toluenesulfonic, tartaric, and trifluoroacetic acids. The chloride salt is particularly preferred for medical purposes. Suitable pharmaceutically acceptable base salts include ammonium salts, alkali metal salts such as sodium and potassium salts, and alkaline earth salts such as magnesium and calcium salts.

The anions useful in the present invention are, of course, also required to be pharmaceutically acceptable and are also selected from the above list.

The compounds useful in the present invention can be presented with an acceptable carrier in the form of a pharmaceutical composition. The carrier must, of course, be acceptable in the sense of being compatible with the other ingredients of the composition and must not be deleterious to the recipient. The carrier can be a solid or a liquid, or both, and is preferably formulated with the compound as a unit-dose composition, for example, a tablet, which can contain from 0.05% to 95% by weight of the active compound. Other pharmacologically active substances can also be present, including other compounds of the present invention. The pharmaceutical compositions of the invention can be prepared by any of the well known techniques of pharmacy, consisting essentially of admixing the components.

Optionally, the combination of the present invention can comprise a composition comprising an ileal bile acid transport inhibiting compound and a bile acid sequestering compound. In such a composition, the CETP inhibiting compound and the bile acid sequestering compound can be present in a single dosage form, for example a pill, a capsule, or a liquid which contains both of the compounds.

These compounds can be administered by any conventional means available for use in conjunction with pharmaceuticals, either as individual therapeutic compounds or as a combination of therapeutic compounds.

The amount of compound which is required to achieve the desired biological effect will, of course, depend on a number of factors such as the specific compound chosen, the use for which it is intended, the mode of administration, and the clinical condition of the recipient.

For a CETP inhibitor, a daily dose of about 0.01 to about 100 mg/kg body weight/day, and preferably between about 0.5 to about 20 mg/kg body weight/day, may generally be appropriate.

For a bile acid sequestrant, a total daily dose can be in the range of from about 1,000 to about 30,000 mg/day, and preferably from about 5,000 to about 15,000 mg/day in a single or a divided dose.

The daily doses described in the preceding paragraphs for the various therapeutic compounds can be administered to the patient in a single dose, or in proportionate multiple subdoses. Subdoses can be administered 2 to 6 times per day. Doses can be in sustained release form effective to obtain desired results.

In the case of pharmaceutically acceptable salts, the weights indicated above refer to the weight of the acid equivalent or the base equivalent of the therapeutic compound derived from the salt.

Oral delivery of the combinations of the present invention can include formulations, as are well known in the art, to provide prolonged or sustained delivery of the drug to the gastrointestinal tract by any number of mechanisms. These include, but are not limited to, pH sensitive release from the dosage form based on the changing pH of the small. intestine, slow erosion of a tablet or capsule, retention in the stomach based on the physical properties of the formulation, bioadhesion of the dosage form to the mucosal lining of the intestinal tract, or enzymatic release of the active drug from the dosage form. For some of the therapeutic compounds useful in the present invention the intended effect is to extend the time period over which the active drug molecule is delivered to the site of action by manipulation of the dosage form. Thus, enteric-coated and enteric-coated controlled release formulations are within the scope of the present invention. Suitable enteric coatings include cellulose acetate phthalate, polyvinylacetate phthalate, hydroxypropylmethylcellulose phthalate and anionic polymers of methacrylic acid and methacrylic acid methyl ester. In another embodiment, when a bile acid sequestrant is used in a combination of the present invention, the bile acid sequestrant can be provided in the form of a liquid, a solid dispersed in a liquid, or in a capsule.

The combinations of the present invention can be delivered orally either in a solid, in a semi-solid, or in a liquid form. When in a liquid or in a semi-solid form, the combinations of the present invention can, for example, be in the form of a liquid, syrup, or contained in a gel capsule (e.g., a gel cap). In one embodiment, when a CETP inhibitor is used in a combination of the present invention, the CETP inhibitor can be provided in the form of a liquid, syrup, or contained in a gel capsule.

For a CETP inhibitor the intravenously administered dose can, for example, be in the range of from about 0.003 mg/kg body weight to about 1.0 mg/kg body weight, preferably from about 0.01 mg/kg body weight to about 0.75 mg/kg body weight, more preferably from about 0.1 mg/kg body weight to about 0.6 mg/kg body weight.

The dose of any of these therapeutic compounds can be conveniently administered as an infusion of from about 10 ng/kg body weight to about 100 ng/kg body weight per minute. Infusion fluids suitable for this purpose can contain, for example, from about 0.1 ng to about 10 mg, preferably from about 1 ng to about 10 mg per milliliter. Unit doses can contain, for example, from about 1 mg to about 10 g of the compound of the present invention. Thus, ampoules for injection can contain, for example, from about 1 mg to about 100 mg.

Pharmaceutical compositions according to the present invention include those suitable for oral, rectal, topical, buccal (e.g., sublingual), and parenteral (e.g., subcutaneous, intramuscular, intradermal, or intravenous) administration, although the most suitable route in any given case will depend on the nature and severity of the condition being treated and on the nature of the particular compound which is being used. In most cases, the preferred route of administration is oral. Typically a bile acid sequestering agent is delivered orally.

Pharmaceutical compositions suitable for oral administration can be presented in discrete units, such as capsules, cachets, lozenges, or tablets, each containing a predetermined amount of at least one therapeutic compound useful in the present invention; as a powder or granules; as a solution or a suspension in an aqueous or non-aqueous liquid; or as an oil-in-water or water-in-oil emulsion. As indicated, such compositions can be prepared by any suitable method of pharmacy which includes the step of bringing into association the active compound(s) and the carrier (which can constitute one or more accessory ingredients). In general, the compositions are prepared by uniformly and intimately admixing the active compound with a liquid or finely divided solid carrier, or both, and then, if necessary, shaping the product. For example, a tablet can be prepared by compressing or molding a powder or granules of the compound, optionally with one or more assessory ingredients. Compressed tablets can be prepared by compressing, in a suitable machine, the compound in a free-flowing form, such as a powder or granules optionally mixed with a binder, lubricant, inert diluent and/or surface active/dispersing agent (s). Molded tablets can be made by molding, in a suitable machine, the powdered compound moistened with an inert liquid diluent.

Pharmaceutical compositions suitable for buccal (sublingual) administration include lozenges comprising a compound of the present invention in a flavored base, usually sucrose, and acacia or tragacanth, and pastilles comprising the compound in an inert base such as gelatin. and glycerin or sucrose and acacia.

Pharmaceutical compositions suitable for parenteral administration conveniently comprise sterile aqueous preparations of a compound of the present invention. These preparations are preferably administered intravenously, although administration can also be effected by means of subcutaneous, intramuscular, or intradermal injection. Such preparations can conveniently be prepared by admixing the compound with water and rendering the resulting solution sterile and isotonic with the blood. Injectable compositions according to the invention will generally contain from 0.1 to 5% w/w of a compound disclosed herein.

Pharmaceutical compositions suitable for rectal administration are preferably presented as unit-dose suppositories. These can be prepared by admixing a compound of the present invention with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which can be used include petroleum jelly (e.g., Vaseline), lanolin, polyethylene glycols, alcohols, and combinations of two or more thereof. The active compound is generally present at a concentration of from 0.1 to 50% w/w of the composition, for example, from 0.5 to 2%.

Transdermal administration is also possible. Pharmaceutical compositions suitable for transdermal administration can be presented as discrete patches adapted to remain in intimate contact with the epidermis of the recipient for a prolonged period of time. Such patches suitably contain a compound of the present invention in an optionally buffered, aqueous solution, dissolved and/or dispersed in an adhesive, or dispersed in a polymer. A suitable concentration of the active compound is about 1% to 35%, preferably about 3% to 15%. As one particular possibility, the compound can be delivered from the patch by electrotransport or iontophoresis, for example, as described in *Pharmaceutical Research*, 3(6), 318 (1986).

In any case, the amount of active ingredient that can be combined with carrier materials to produce a single dosage form to be administered will vary depending upon the host treated and the particular mode of administration.

The solid dosage forms for oral administration including capsules, tablets, pills, powders, gel caps, and granules noted above comprise one or more compounds useful in the present invention admixed with at least one inert diluent such as sucrose, lactose, or starch. Such dosage forms may also comprise, as in normal practice, additional substances other than inert diluents, e.g., lubricating agents such as magnesium stearate or solubilizing agents such as cyclodextrins. In the case of capsules, tablets, powders, granules, gel caps, and pills, the dosage forms may also comprise buffering agents. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

Injectable preparations, for example, sterile injectable aqueous or oleaginous suspensions may be formulated according to the known art using suitable dispersing or setting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Pharmaceutically acceptable carriers encompass all the foregoing and the like.

In combination therapy, administration of two or more of the therapeutic agents useful in the present invention may take place sequentially in separate formulations, or may be accomplished by simultaneous administration in a single formulation or separate formulations. Administration may be accomplished by oral route, or by intravenous, intramuscular, or subcutaneous injections. The formulation may be in the form of a bolus, or in the form of aqueous or non-aqueous isotonic sterile injection solutions or suspensions. These solutions and suspensions may be prepared from sterile powders or granules having one or more pharmaceutically-acceptable carriers or diluents, or a binder such as gelatin or hydroxypropylmethyl cellulose, together with one or more of a lubricant, preservative, surface active or dispersing agent.

For oral administration, the pharmaceutical composition may be in the form of, for example, a tablet, capsule, suspension, or liquid. Capsules, tablets, etc., can be prepared by conventional methods well known in the art. The pharmaceutical composition is preferably made in the form of a dosage unit containing a particular amount of the active ingredient or ingredients. Examples of dosage units are tablets or capsules. These may with advantage contain one or more therapeutic compound in an amount described above. For example, in the case of a CETP inhibitor, the dose range may be from about 0.01 mg to about 500 mg or any other dose, dependent upon the specific inhibitor, as is known in the art. In the case of an bile acid sequestrant the dose range can be from about 1,000 mg to about 30,000 mg or any other dose, dependent upon the specific bile acid sequestrant, as is known in the art.

The active ingredients may also be administered by injection as a composition wherein, for example, saline, dextrose, or water may be used as a suitable carrier. A suitable daily dose of each active therapeutic compound is one that achieves the same blood serum level as produced by oral administration as described above.

The therapeutic compounds may further be administered by any combination of oral/oral, oral/parenteral, or parenteral/parenteral route.

Pharmaceutical compositions for use in the treatment methods of the present invention may be administered in oral form or by intravenous administration. Oral administration of the combination therapy is preferred. Dosing for oral administration may be with a regimen calling for single daily dose, or for a single dose every other day, or for multiple, spaced doses throughout the day. The therapeutic compounds which make up the combination therapy may be administered simultaneously, either in a combined dosage form or in separate dosage forms intended for substantially simultaneous oral administration. The therapeutic compounds which make up the combination therapy may also be administered sequentially, with either therapeutic compound being administered by a regimen calling for two-step ingestion. Thus, a regimen may call for sequential administration of the therapeutic compounds with spaced-apart ingestion of the separate, active agents. The time period between the multiple ingestion steps may range from a few minutes to several hours, depending upon the properties of each therapeutic compound such as potency, solubility, bioavailability, plasma half-life and kinetic profile of the therapeutic compound, as well as depending upon the effect of food ingestion and the age and condition of the patient. Circadian variation of the target molecule concentration may also determine the optimal dose interval. The therapeutic compounds of the combined therapy whether administered simultaneously, substantially simultaneously, or sequentially, may involve a regimen calling for administration of one therapeutic compound by oral route and another therapeutic compound by intravenous route. Whether the therapeutic compounds of the combined therapy are administered by oral or intravenous route, separately or together, each such therapeutic compound will be contained in a suitable pharmaceutical formulation of pharmaceutically-acceptable excipients, diluents or other formulations components. Examples of suitable pharmaceutically-acceptable formulations containing the therapeutic compounds for oral administration are given above.

Treatment Regimen

The dosage regimen to prevent, give relief from, or ameliorate a disease condition having hyperlipidemia as an element of the disease, e.g., atherosclerosis, or to protect against or treat further high cholesterol plasma or blood levels with the compounds and/or compositions of the present invention is selected in accordance with a variety of factors. These include the type, age, weight, sex, diet, and medical condition of the patient, the severity of the disease, the route of administration, pharmacological considerations such as the activity, efficacy, pharmacokinetics and toxicology profiles of the particular compound employed, whether a drug delivery system is utilized, and whether the compound is administered as part of a drug combination. Thus, the dosage regimen actually employed may vary widely and therefore deviate from the preferred dosage regimen set forth above.

Initial treatment of a patient suffering from a hyperlipidemic condition can begin with the dosages indicated above. Treatment should generally be continued as necessary over a period of several weeks to several months or years until the hyperlipidemic disease condition has been controlled or eliminated. Patients undergoing treatment with the compounds or compositions disclosed herein can be routinely monitored by, for example, measuring serum LDL and total cholesterol levels by any of the methods well known in the art, to determine the effectiveness of the combination therapy. Continuous analysis of such data permits modification of the treatment regimen during therapy so that optimal effective amounts of each type of therapeutic compound are administered at any point in time, and so that the duration of treatment can be determined as well. In this way, the treatment regimen/dosing schedule can be rationally modified over the course of therapy so that the lowest amount of the therapeutic compounds which together exhibit satisfactory effectiveness is administered, and so that administration is continued only so long as is necessary to successfully treat the hyperlipidemic condition.

A potential advantage of the combination therapy disclosed herein may be reduction of the amount of any individual therapeutic compound, or all therapeutic compounds, effective in treating hyperlipidemic conditions such as atherosclerosis and hypercholesterolemia.

One of the several embodiments of the present invention comprises a combination therapy comprising the use of a first amount of an CETP inhibitor and a second amount of another cardiovascular therapeutic useful in the prophylaxis or treatment of hyperlipidemia or atherosclerosis, wherein said first and second amounts together comprise an anti-hyperlipidemic condition effective amount or an anti-atherosclerotic condition effective amount of said compounds. For example one of the many embodiments of the present invention is a combination therapy comprising therapeutic dosages of an CETP inhibitor and a bile acid sequestering agent.

The following non-limiting examples serve to illustrate various aspects of the present invention.

C. EXAMPLES

Table 3 illustrates examples of some combinations of the present invention wherein the combination comprises a first amount of a CETP inhibitor and a second amount of a bile acid sequestration agent, wherein said first and second amounts together comprise an anti-hyperlipidemic condition effective amount or an anti-atherosclerotic condition effective amount of said compounds.

TABLE 3

| Example Number | Component 1 | Component 2 |
| --- | --- | --- |
| 5501 | C-1 | cholestyramine |
| 5502 | C-2 | cholestyramine |
| 5503 | C-3 | cholestyramine |
| 5504 | C-4 | cholestyramine |
| 5505 | C-5 | cholestyramine |
| 5506 | C-6 | cholestyramine |
| 5507 | C-7 | cholestyramine |
| 5508 | C-8 | cholestyramine |
| 5509 | C-9 | cholestyramine |
| 5510 | C-10 | cholestyramine |
| 5511 | C-11 | cholestyramine |
| 5512 | C-12 | cholestyramine |
| 5513 | C-13 | cholestyramine |
| 5514 | C-14 | cholestyramine |
| 5515 | C-15 | cholestyramine |
| 5516 | C-16 | cholestyramine |
| 5517 | C-17 | cholestyramine |
| 5518 | C-18 | cholestyramine |
| 5519 | C-19 | cholestyramine |
| 5520 | C-20 | cholestyramine |
| 5521 | C-1 | colestipol |
| 5522 | C-2 | colestipol |
| 5523 | C-3 | colestipol |
| 5524 | C-4 | colestipol |
| 5525 | C-5 | colestipol |
| 5526 | C-6 | colestipol |
| 5527 | C-7 | colestipol |
| 5528 | C-8 | colestipol |
| 5529 | C-9 | colestipol |
| 5530 | C-10 | colestipol |
| 5531 | C-11 | colestipol |
| 5532 | C-12 | colestipol |
| 5533 | C-13 | colestipol |
| 5534 | C-14 | colestipol |
| 5535 | C-15 | colestipol |
| 5536 | C-16 | colestipol |
| 5537 | C-17 | colestipol |
| 5538 | C-18 | colestipol |
| 5539 | C-19 | colestipol |
| 5540 | C-20 | colestipol |
| 5541 | C-1 | knedel A |
| 5542 | C-2 | knedel A |
| 5543 | C-3 | knedel A |
| 5544 | C-4 | knedel A |
| 5545 | C-5 | knedel A |
| 5546 | C-6 | knedel A |
| 5547 | C-7 | knedel A |
| 5548 | C-8 | knedel A |
| 5549 | C-9 | knedel A |
| 5550 | C-10 | knedel A |
| 5551 | C-11 | knedel A |
| 5552 | C-12 | knedel A |
| 5553 | C-13 | knedel A |
| 5554 | C-14 | knedel A |
| 5555 | C-15 | knedel A |
| 5556 | C-16 | knedel A |
| 5557 | C-17 | knedel A |
| 5558 | C-18 | knedel A |
| 5559 | C-19 | knedel A |
| 5560 | C-20 | knedel A |
| 5561 | C-1 | knedel B |
| 5562 | C-2 | knedel B |
| 5563 | C-3 | knedel B |
| 5564 | C-4 | knedel B |
| 5565 | C-5 | knedel B |
| 5566 | C-6 | knedel B |
| 5567 | C-7 | knedel B |
| 5568 | C-8 | knedel B |
| 5569 | C-9 | knedel B |
| 5570 | C-10 | knedel B |
| 5571 | C-11 | knedel B |
| 5572 | C-12 | knedel B |
| 5573 | C-13 | knedel B |
| 5574 | C-14 | knedel B |
| 5575 | C-15 | knedel B |
| 5576 | C-16 | knedel B |
| 5577 | C-17 | knedel B |
| 5578 | C-18 | knedel B |
| 5579 | C-19 | knedel B |
| 5580 | C-20 | knedel B |
| 5580.1 | C-1 | S-3 |
| 5580.2 | C-2 | S-3 |
| 5580.3 | C-3 | S-3 |
| 5580.4 | C-4 | S-3 |
| 5580.5 | C-5 | S-3 |
| 5580.6 | C-6 | S-3 |
| 5580.7 | C-7 | S-3 |
| 5580.8 | C-8 | S-3 |
| 5580.9 | C-9 | S-3 |
| 5580.10 | C-10 | S-3 |
| 5580.11 | C-11 | S-3 |
| 5580.12 | C-12 | S-3 |
| 5580.13 | C-13 | S-3 |
| 5580.14 | C-14 | S-3 |
| 5580.15 | C-15 | S-3 |
| 5580.16 | C-16 | S-3 |
| 5580.17 | C-17 | S-3 |
| 5580.18 | C-18 | S-3 |
| 5580.19 | C-19 | S-3 |
| 5580.20 | C-20 | S-3 |
| 5580.21 | C-1 | CholestaGel |
| 5580.22 | C-2 | CholestaGel |
| 5580.23 | C-3 | CholestaGel |
| 5580.24 | C-4 | CholestaGel |
| 5580.25 | C-5 | CholestaGel |
| 5580.26 | C-6 | CholestaGel |
| 5580.27 | C-7 | CholestaGel |
| 5580.28 | C-8 | CholestaGel |
| 5580.29 | C-9 | CholestaGel |
| 5580.30 | C-10 | CholestaGel |
| 5580.31 | C-11 | CholestaGel |
| 5580.32 | C-12 | CholestaGel |
| 5580.33 | C-13 | CholestaGel |
| 5580.34 | C-14 | CholestaGel |
| 5580.35 | C-15 | CholestaGel |

TABLE 3-continued

| Example Number | Component 1 | Component 2 |
|---|---|---|
| 5580.36 | C-16 | CholestaGel |
| 5580.37 | C-17 | CholestaGel |
| 5580.38 | C-18 | CholestaGel |
| 5580.39 | C-19 | CholestaGel |
| 5580.40 | C-20 | CholestaGel |
| 5580.41 | C-1 | OmegaGel |
| 5580.42 | C-2 | OmegaGel |
| 5580.43 | C-3 | OmegaGel |
| 5580.44 | C-4 | OmegaGel |
| 5580.45 | C-5 | OmegaGel |
| 5580.46 | C-6 | OmegaGel |
| 5580.47 | C-7 | OmegaGel |
| 5580.48 | C-8 | OmegaGel |
| 5580.49 | C-9 | OmegaGel |
| 5580.50 | C-10 | OmegaGel |
| 5580.51 | C-11 | OmegaGel |
| 5580.52 | C-12 | OmegaGel |
| 5580.53 | C-13 | OmegaGel |
| 5580.54 | C-14 | OmegaGel |
| 5580.55 | C-15 | OmegaGel |
| 5580.56 | C-16 | OmegaGel |
| 5580.57 | C-17 | OmegaGel |
| 5580.58 | C-18 | OmegaGel |
| 5580.59 | C-19 | OmegaGel |
| 5580.60 | C-20 | OmegaGel |

Biological Assays

The utility of the combinations of the present invention can be shown by the following assays. These assays are performed in vitro and in animal models essentially using procedures recognized to show the utility of the present invention.

In Vitro Assay of Ccompounds that Inhibit IBAT-mediated Uptake of [$^{14}$C]-Taurocholate (TC) in H14 Cells Baby hamster kidney cells (BHK) transfected with the cDNA of human IBAT (H14 cells) are to be seeded at 60,000 cells/well in 96 well Top-Count tissue culture plates for assays run within in 24 hours of seeding, 30,000 cells/well for assays run within 48 hours, and 10,000 cells/well for assays run within 72 hours.

On the day of assay, the cell monolayer is gently washed once with 100 μl assay buffer (Dulbecco's Modified Eagle's medium with 4.5 g/L glucose+0.2% (w/v) fatty acid free bovine serum albumin-(FAF)BSA). To each well 50 μl of a two-fold concentrate of test compound in assay buffer is added along with 50 μl of 6 μM [$^{14}$C]-taurocholate in assay buffer (final concentration of 3 μM [$^{14}$C]-taurocholate). The cell culture plates are incubated 2 hours at 37° C. prior to gently washing each well twice with 100 μl 4° C. Dulbecco's phosphate-buffered saline (PBS) containing 0.2% (w/v) (FAF)BSA. The wells are then to be gently washed once with 100 μl 4° C. PBS without (FAF)BSA. To each 200 μl of liquid scintillation counting fluid is to be added, the plates are heat sealed and shaken for 30 minutes at room temperature prior to measuring the amount of radioactivity in each well on a Packard Top-Count instrument.

In Vitro Assay of Compounds that Inhibit Uptake of [$^{14}$C]-Alanine

The alanine uptake assay can be performed in an identical fashion to the taurocholate assay, with the exception that labeled alanine is to be substituted for the labeled taurocholate.

In Vivo Assay of Compounds that Inhibit Rat Ileal Uptake of [$^{14}$C]-Taurocholate into Bile (See "Metabolism of 3α, 7β-dihydroxy-7α-methyl-5β-cholanoic acid and 3α, 7β-dihydroxy-7α-methyl-5β-cholanoic acid in hamsters" in *Biochimica et Biophysica Acta*, 833, 196–202 (1985) by Une et al., herein incorporated by reference.)

Male wistar rats (200–300 g) are to be anesthetized with inactin @100 mg/kg. Bile ducts are cannulated with a 10" length of PE10 tubing. The small intestine is exposed and laid out on a gauze pad. A canulae (⅛" luer lock, tapered female adapter) is inserted at 12 cm from the junction of the small intestine and the cecum. A slit is cut at 4 cm from this same junction (utilizing a 8 cm length of ileum). 20 ml of warm Dulbecco's phosphate buffered saline, pH 6.5 (PBS) is used to flush out the intestine segment. The distal opening is cannulated with a 20 cm length of silicone tubing (0.02" I.D.×0.037" O.D.). The proximal cannulae is hooked up to a peristaltic pump and the intestine is washed for 20 min with warm PBS at 0.25 ml/min. Temperature of the gut segment is to be monitored continuously. At the start of the experiment, 2.0. ml of control sample ([$^{14}$C]-taurocholate @ 0.05 mCi/ml with 5 mM non-radiolabeled taurocholate) is loaded into the gut segment with a 3 ml syringe and bile sample collection is begun. Control sample is infused at a rate of 0.25 ml/min for 21 min. Bile samples fractions will be collected every 3 minute for the first 27 minutes of the procedure. After the 21 min of sample infusion, the ileal loop is washed out with 20 ml of warm PBS (using a 30 ml syringe), and then the loop is washed out for 21 min with warm PBS at 0.25 ml/min. A second perfusion is to be initiated as described above but with test compound being administered as well (21 min administration followed by 21 min of wash out) and bile to be sampled every 3 min for the first 27 min. If necessary, a third perfusion will be performed as above that typically contains the control sample.

Measurement of Hepatic Cholesterol Concentration (HEPATIC CHOL)

Liver tissue is to be weighed and homogenized in chloroform:methanol (2:1). After homogenization and centrifugation the supernatant is separated and dried under nitrogen. The residue is to be dissolved in isopropanol and the cholesterol content will be measured enzymatically, using a combination of cholesterol oxidase and peroxidase, as described by Allain, C. A. et al., *Clin. Chem.*, 20, 470 (1974) (herein incorporated by reference).

Measurement of Hepatic HMG CoA-Reductase Activity (HMG COA)

Hepatic microsomes are to be prepared by homogenizing liver samples in a phosphate/sucrose buffer, followed by centrifugal separation. The final pelleted material is resuspended in buffer and an aliquot will be assayed for HMG CoA reductase activity by incubating for 60 minutes at 37° C. in the presence of $^{14}$C-HMG-COA (Dupont-NEN). The reaction is stopped by adding 6N HCl followed by centrifugation. An aliquot of the supernatant is separated, by thin-layer chromatography, and the spot corresponding to the enzyme product is scraped off the plate, extracted and radioactivity is determined by scintillation counting. (Reference: Akerlund, J. and Bjorkhem, I. (1990) *J. Lipid Res.* 31, 2159).

Determination of Serum Cholesterol (SER.CHOL, HDL-CHOL, TGI and VLDL+LDL)

Total serum cholesterol (SER.CHOL) are to be measured enzymatically using a commercial kit from Wako Fine Chemicals (Richmond, Va.); Cholesterol C11, Catalog No. 276–64909. HDL cholesterol (HDL-CHOL) will be assayed using this same kit after precipitation of VLDL and LDL with Sigma Chemical Co. HDL Cholesterol reagent, Catalog No. 352-3 (dextran sulfate method). Total serum triglycerides (blanked) (TGI) will be assayed enzymatically with Sigma Chemical Co. GPO-Trinder, Catalog No. 337-B. VLDL and LDL (VLDL +LDL) cholesterol concentrations will be calculated as the difference between total and HDL cholesterol.

Measurement of Hepatic Cholesterol 7-α-Hydroxylase Activity (7a-OHase)

Hepatic microsomes are to be prepared by homogenizing liver samples in a phosphate/sucrose buffer, followed by centrifugal separation. The final pelleted material is resuspended in buffer and an aliquot will be assayed for cholesterol 7-α-hydroxylase activity by incubating for 5 minutes at 37° C. in the presence of NADPH. Following extraction into petroleum ether, the organic solvent is evaporated and the residue is dissolved in acetonitrile/methanol. The enzymatic product will be separated by injecting an aliquot of the extract onto a $C_{18}$ reversed phase HPLC column and quantitating the eluted material using UV detection at 240 nm. (Reference: Horton, J. D., et al. (1994) *J. Clin. Invest.* 93, 2084).

Rat Gavage Assay

Male Wister rats (275–300 g) are to be administered IBAT inhibitors using an oral gavage procedure. Drug or vehicle (0.2% TWEEN 80 in water) is administered once a day (9:00–10:0 a.m.) for 4 days at varying dosages in a final volume of 2 mL per kilogram of body weight. (TWEEN 80 is a 20 molar polyethyleneoxide sorbitan monooleate surfactant manufactured by ICI Specialty Chemicals, Wilmington, Del., U.S.A.) Total fecal samples are collected during the final 48 hours of the treatment period and analyzed for bile acid content using an enzymatic assay as described below. Compound efficacy will be determined by comparison of the increase in fecal bile acid (FBA) concentration in treated rats to the mean FBA concentration of rats in the vehicle group.

Measurement of Fecal Bile Acid Concentration (FBA)

Total fecal output from individually housed rats is to be collected for 24 or 48 hours, dried under a stream of nitrogen, pulverized and weighed. Approximately 0.1 gram is weighed out and extracted into an organic solvent (butanol/water). Following separation and drying, the residue is dissolved in methanol and the amount of bile acid present will be measured enzymatically using the 3α-hydroxysteroid steroid dehydrogenase reaction with bile acids to reduce NAD. (see Mashige, F. et al. *Clin. Chem.,* 27, 1352 (1981), herein incorporated by reference).

[$^3$H]taurocholate Uptake in Rabbit Brush Border Membrane Vesicles (BBMV)

Rabbit Ileal brush border membranes are to be prepared from frozen ileal mucosa by the calcium precipitation method describe by Malathi et al. (*Biochimica Biophysica Acta,* 554, 259 (1979), herein incorporated by reference). The method for measuring taurocholate is essentially as described by Kramer et al. (*Biochimica Biophysica Acta,* 1111, 93 (1992), herein incorporated by reference) except the assay volume will be 200 µl instead of 100 µl. Briefly, at room temperature a 190 µl solution containing 2 µM [$^3$H]-taurocholate(0.75 µCi), 20 mM tris, 100 mM NaCl, 100 mM mannitol pH 7.4 is incubated for 5 sec with 10 µl of brush border membrane vesicles (60–120 µg protein). The incubation is initiated by the addition of the BBMV while vortexing and the reaction is to be stopped by the addition of 5 ml of ice cold buffer (20 mM Hepes-tris, 150 mM KCl) followed immediately by filtration through a nylon filter (0.2 µm pore) and an additional 5 ml wash with stop buffer.

Acyl-CoA; Cholesterol Acyl Transferase (ACAT)

Hamster liver and rat intestinal microsomes are to be prepared from tissue as described previously (*J. Biol. Chem.,* 255, 9098 (1980), herein incorporated by reference) and used as a source of ACAT enzyme. The assay will consist of a 2.0 ml incubation containing 24 µM Oleoyl-CoA (0.05 µCi) in a 50 mM sodium phosphate, 2 mM DTT ph 7.4 buffer containing 0.25% BSA and 200 µg of microsomal protein. The assay will be initiated by the addition of oleoyl-CoA. The reaction proceeds for 5 min at 37° C. and will be terminated by the addition of 8.0 ml of chloroform/methanol (2:1). To the extraction is added 125 µg of cholesterol oleate in chloroform methanol to act as a carrier and the organic and aqueous phases of the extraction are separated by centrifugation after thorough vortexing. The chloroform phase is to be taken to dryness and then spotted on a silica gel 60 TLC plate and developed in hexane/ethyl ether (9:1). The amount of cholesterol ester formed will be determined by measuring the amount of radioactivity incorporated into the cholesterol oleate spot on the TLC plate with a Packard Instaimager.

Dog Model for Evaluating Lipid Lowering Drugs

Male beagle dogs, obtained from a vendor such as Marshall farms and weighing 6–12 kg are fed once a day for two hours and given water ad libitum. Dogs may be randomly assigned to a dosing groups consisting of 6 to 12 dogs each, such as: vehicle, i.g.; 1 mg/kg, i.g.; 2 mg/kg, i.g.; 4 mg/kg, i.g.; 2 mg/kg, p.o. (powder in capsule). Intra-gastric dosing of a therapeutic material dissolved in aqueous solution (for example, 0.2% Tween 80 solution [polyoxyethylene monooleate, Sigma Chemical Co., St. Louis, Mo.]) may be done using a gavage tube. Prior to initiating dosing, blood samples may be drawn from the cephalic vein in the morning before feeding in order to evaluate serum cholesterol (total and HDL) and triglycerides. For several consecutive days animals are dosed in the morning, prior to feeding. Animals are to be allowed 2 hours to eat before any remaining food is removed. Feces are to be collected over a 2 day period at the end of the study and may be analyzed for bile acid or lipid content. Blood samples are also to be taken, at the end of the treatment period, for comparison with pre-study serum lipid levels. Statistical significance will be determined using the standard student's T-test with p<0.05.

Dog Serum Lipid Measurement

Blood is to be collected from the cephalic vein of fasted dogs in serum separator tubes (Vacutainer SST, Becton Dickinson and Co., Franklin Lakes, N.J.). The blood is centrifuged at 2000 rpm for 20 minutes and the serum decanted.

Total cholesterol may be measured in a 96 well format using a Wako enzymatic diagnostic kit (Cholesterol CII) (Wako Chemicals, Richmond, Va.), utilizing the cholesterol oxidase reaction to produce hydrogen peroxide which is measured calorimetrically. A standard curve from 0.5 to 10 µg cholesterol is to be prepared in the first 2 columns of the plate. The serum samples (20–40 µl, depending on the expected lipid concentration) or known serum control samples are added to separate wells in duplicate. Water is added to bring the volume to 100 µl in each well. A 100 µl aliquot of color reagent is added to each well and the plates will be read at 500 nm after a 15 minute incubation at 37 degrees centigrade.

HDL cholesterol may be assayed using Sigma kit No. 352-3 (Sigma Chemical Co., St. Louis, Mo.) which utilizes dextran sulfate and Mg ions to selectively precipitate LDL and VLDL. A volume of 150 µl of each serum sample is to be added to individual microfuge tubes, followed by 15 µl of HDL cholesterol reagent (Sigma 352-3). Samples are to be mixed and centrifuged at 5000 rpm for 5 minutes. A 50 µl aliquot of the supernatant is to be then mixed with 200 µl of saline and assayed using the same procedure as for total cholesterol measurement.

Triglycerides are to be measured using Sigma kit No. 337 in a 96 well plate format. This procedure will measure glycerol, following its release by reaction of triglycerides with lipoprotein lipase. Standard solutions of glycerol (Sigma 339-11) ranging from 1 to 24 µg are to be used to generate the standard curve. Serum samples (20–40 µl, depending on the expected lipid concentration) are added to wells in duplicate. Water is added to bring the volume to 100 µl in each well and 100 µl of color reagent is also added to each well. After mixing and a 15 minute incubation, the plates will be read at 540 nm and the triglyceride values calculated from the standard curve. A replicate plate is also to be run using a blank enzyme reagent to correct for any endogenous glycerol in the serum samples.

Dog Fecal Bile Acid Measurement

Fecal samples may be collected to determine the fecal bile acid (FBA) concentration for each animal. Fecal collections may be made during the final 48 hours of the study, for two consecutive 24 hour periods between 9:00 am and 10:00 am each day, prior to dosing and feeding. The separate two day collections from each animal are to be weighed, combined and homogenized with distilled water in a processor (Cuisinart) to generate a homogeneous slurry. About 1.4 g of the homogenate is to be extracted in a final concentration of 50% tertiary butanol/distilled water (2:0.6) for 45 minutes in a 37° C. water bath and centrifuged for 13 minutes at 2000×g. The concentration of bile acids (mmoles/day) may be determined using a 96-well enzymatic assay system (1,2). A 20 µl aliquot of the fecal extract is to be added to two sets each of triplicate wells in a 96-well assay plate. A standardized sodium taurocholate solution and a standardized fecal extract solution (previously made from pooled samples and characterized for its bile acid concentration) will also analyzed for assay quality control. Twenty-microliter aliquots of sodium taurocholate, serially diluted to generate a standard curve are similarly to be added to two sets of triplicate wells. A 230 µl reaction mixture containing 1M hydrazine hydrate, 0.1 M pyrophosphate and 0.46 mg/ml NAD is to be added to each well. A 50 µl aliquot of 3a-hydroxysteroid dehydrogenase enzyme (HSD; 0.8 units/ml) or assay buffer (0.1 M sodium pyrophosphate) are then added to one of the two sets of triplicates. All reagents may be obtained from Sigma Chemical Co., St. Louis, Mo. Following 60 minutes of incubation at room temperature, the optical density at 340 nm will be measured and the mean of each set of triplicate samples will be calculated. The difference in optical density±HSD enzyme is to be used to determine the bile acid concentration (mM) of each sample based on the sodium taurocholate standard curve. The bile acid concentration of the extract, the weight of the fecal homogenate (grams) and the body weight of the animal are to be used to calculate the corresponding FBA concentration in mmoles/kg/day for each animal. The mean FBA concentration (mmoles/kg/day) of the vehicle group is to be subtracted from the FBA concentration of each treatment group to determine the increase (delta value) in FBA concentration as a result of the treatment.

CETP Activity Assay in Human Plasma (Tritiated Cholesteryl Ester)

Blood is to be obtained from healthy volunteers. Blood is collected in tubes containing EDTA (EDTA plasma pool). The EDTA human plasma pool previously stored at −20° C., is to be thawed at room temperature, and centrifuged for 5 minutes to remove any particulate matter. Tritiated HDL, radiolabeled in the cholesteryl ester moiety ([$^3$H]CE-HDL) as described by Morton and Zilversmit (*J. Biol. Chem.*, 256, 11992–95 (1981)), is to be added to the plasma to a final concentration of (25 µg/ml cholesterol). Inhibitor compounds are to be added to the plasma as follows: Equal volumes of the plasma containing the [$^3$H]CE-HDL (396 µl) are added by pipette into micro tubes (Titertube®, Bio-Rad laboratories, Hercules, Calif.). Compounds, usually dissolved as 20–50 mM stock solutions in DMSO, are to be serially diluted in DMSO (or an alternative solvent in some cases, such as dimethylformamide or ethanol). Four µl of each of the serial dilutions of inhibitor compounds or DMSO alone are then added to each of the plasma tubes. The tubes are immediately mixed. Triplicate aliquots (100 µl) from each plasma tube are then transferred to wells of 96-well round-bottomed polystyrene microtiter plates (Corning, Corning, N.Y.). Plates are sealed with plastic film and incubated at 37° C. for 4 hours. Test wells are to contain plasma with dilutions of inhibitor compounds. Control wells are to contain plasma with DMSO alone. Blank wells are to contain plasma with DMSO alone that are left in the micro tubes at 4° C. for the 4 hour incubation and are added to the microtiter wells at the end of the incubation period. VLDL and LDL are precipitated by the addition of 10 µl of precipitating reagent (1% (w/v) dextran sulfate (Dextralip50)/0.5 M magnesium chloride, pH 7.4) to all wells. The wells are mixed on a plate mixer and then incubated at ambient temperature for 10 min. The plates are then centrifuged at 1000×g for 30 min at 10° C. The supernatants (50 µl) from each well are then transferred to Picoplate™ 96 plate wells (Packard, Meriden, Conn.) containing 250:1 Microscint™-40 (Packard, Meriden, Conn.). The plates are heat-sealed (TopSeal™-P, Packard, Meriden Conn.) according to the manufacturer's directions and mixed for 30 min. Radioactivity will be measured on a microplate scintillation counter (TopCount, Packard, Meriden, Conn.). IC$_{50}$ values will be determined as the concentration of inhibitor compound inhibiting transfer of [$^3$H]CE from the supernatant [$^3$H]CE-HDL to the precipitated VLDL and LDL by 50% compared to the transfer obtained in the control wells. The maximum percentage transfer (in the control wells) will be determined using the following equation:

$$\% \text{ Transfer} = \frac{[dpm_{blank} - dpm_{control}] \times 100}{dpm_{blank}}$$

The percentage of control transfer determined in the wells containing inhibitor compounds is determined as follows:

$$\% \text{ Control} = \frac{[dpm_{blank} - dpm_{test}] \times 100}{dpm_{blank} - dpm_{control}}$$

IC$_{50}$ values will be calculated from plots of % control versus concentration of inhibitor compound.

CETP Activity In Vitro

The ability of compounds to inhibit CETP activity are assessed using an in vitro assay that measures the rate of transfer of radiolabeled cholesteryl ester ([$^3$H]CE) from HDL donor particles to LDL acceptor particles. Details of the assay are provided by Glenn et al. (Glenn and Melton, "Quantification of Cholesteryl Ester Transfer Protein (CETP): A) CETP Activity and B) Immunochemical Assay of CETP Protein," *Meth. Enzymol.*, 263, 339–351 (1996)). CETP can be obtained from the serum-free conditioned medium of CHO cells transfected with a cDNA for CETP (Wang, S. et al. *J. Biol. Chem.* 267, 17487–17490 (1992)).

To measure CETP activity, [$^3$H]CE-labeled HDL, LDL, CETP and assay buffer (50 mM tris(hydroxymethyl) aminomethane, pH 7.4; 150 mM sodium chloride; 2 mM ethylenediamine-tetraacetic acid; 1% bovine serum albumin) are incubated in a volume of 200 µl, for 2 hours at 37° C. in 96 well plates. LDL is differentially precipitated by the addition of 50 µl of 1% (w/v) dextran sulfate/0.5 M magnesium chloride, mixed by vortex, and incubated at room temperature for 10 minutes. The solution (200 µl) is transferred to a filter plate (Millipore). After filtration, the radioactivity present in the precipitated LDL is measured by liquid scintillation counting. Correction for non-specific transfer or precipitation is made by including samples that do not contain CETP. The rate of [$^3$H]CE transfer using this assay is linear with respect to time and CETP concentration, up to 25–30% of [$^3$H]CE transferred.

The potency of test compounds can be determined by performing the above described assay in the presence of varying concentrations of the test compounds and determining the concentration required for 50% inhibition of transfer of [$^3$H]CE from HDL to LDL. This value is defined as the $IC_{50}$. the $IC_{50}$ values determined from this assay will be accurate when the $IC_{50}$ is greater than 10 nM. In the case where compounds have greater inhibitory potency, accurate measurements of $IC_{50}$ may be determined using longer incubation times (up to 18 hours) and lower final concentrations of CETP (<50 nM).

Inhibition of CETP Activity In Vivo

Inhibition of CETP activity by a test compound can be determined by administering the compound to an animal by intravenous injection or oral gavage, measuring the amount of transfer of tritium-labeled cholesteryl ester ([$^3$H]CE) from HDL to VLDL and LDL particles, and comparing this amount of transfer with the amount of transfer observed in control animals.

Male golden Syrian hamsters are to be maintained on a diet of chow containing 0.24% cholesterol for at least two weeks prior to the study. For animals receiving intravenous dosing, immediately before the experiment, animals are anesthetized with pentobarbital. Anesthesia is maintained throughout the experiment. In-dwelling catheters are to be inserted into the jugular vein and carotid artery. At the start of the experiment all animals will receive 0.2 ml of a solution containing [$^3$H]CE-HDL into the jugular vein. [$^3$H]CE-HDL is a preparation of human HDL containing tritium-labeled cholesteryl ester, and is prepared according to the method of Glenn et al. (*Meth. Enzymol.*, 263, 339–351 (1996)). Test compound is dissolved as a 80 mM stock solution in vehicle (2% ethanol: 98% PEG 400, Sigma Chemical Company, St. Louis, Mo., USA) and administered either by bolus injection or by continuous infusion. Two minutes after the [$^3$H]CE-HDL dose is administered, animals are to receive 0.1 ml of the test solution injected into the jugular vein. Control animals are to receive 0.1 ml of the intravenous vehicle solution without test compound. After 5 minutes, the first blood samples (0.5 ml) are taken from the carotid artery and collected in standard microtainer tubes containing ethylenediamine tetraacetic acid. Saline (0.5 ml) is injected to flush the catheter and replace blood volume. Subsequent blood samples are to be taken at two hours and four hours by the same method. Blood samples are mixed well and kept on ice until the completion of the experiment. Plasma is obtained by centrifugation of the blood samples at 4° C. The plasma (50 µl) is treated with 5 µl of precipitating reagent (dextran sulfate, 10 g/l; 0.5 M magnesium chloride) to remove VLDL/LDL. After centrifugation, the resulting supernatant (25 µl) containing the HDL will be analyzed for radioactivity using a liquid scintillation counter.

The percentage [$^3$H]CE transferred from HDL to LDL and VLDL (% transfer) will be calculated based on the total radioactivity in equivalent plasma samples before precipitation. Typically, the amount of transfer from HDL to LDL and VLDL in control animals will be 20% to 35% after 4 hours.

Alternatively, conscious, non-anesthetized animals can receive an oral gavage dose of test compound as a suspension in 0.1% methyl cellulose in water. At a time determined for each compound at which plasma levels of the test substance reach their peak ($C_{max}$) after oral dosing, the animals are to be anesthetized with pentobarbital and then dosed with 0.2 ml of a solution containing [$^3$H]CE-HDL into the jugular vein as described above. Control animals are to receive 0.25 ml of the vehicle solution without test compound by oral gavage. After 4 hours, the animals are to be sacrificed, blood samples are collected, and the percentage [$^3$H]CE transferred from HDL to LDL and VLDL (% transfer) is assayed as described above.

Alternatively, inhibition of CETP activity by a test compound can be determined by administering the compound to mice that have been selected for expression of human CETP (hCETP) by transgenic manipulation (hCETP mice). Test compounds can be administered by intravenous injection, or oral gavage and the amount of transfer of tritium-labeled cholesteryl ester ([$^3$H]CE) from HDL to VLDL and LDL particles is determined, and compared to the amount of transfer observed in control animals. C57Bl/6 mice that are homozygous for the hCETP gene are to be maintained on a high fat chow diet, such as TD 88051, as described by Nishina et al. (*J Lipid Res.*, 31, 859–869 (1990)) for at least two weeks prior to the study. Mice are to receive an oral gavage dose of test compound as a suspension in 0.1% methyl cellulose in water or an intravenous bolus injection of test compound in 10% ethanol and 90% polyethylene glycol. Control animals are to receive the vehicle solution without test compound by oral gavage or by an intravenous bolus injection. At the start of the experiment all animals will receive 0.05 ml of a solution containing [$^3$H]CE-HDL into the tail vein. [$^3$H]CE-HDL will be a preparation of human HDL containing tritium-labeled cholesteryl ester, and is prepared according to the method of Glenn et al. (*Meth. Enzymol.*, 263, 339–351 (1996)). After 30 minutes, the animals are exsanguinated and blood collected in standard microtainer tubes containing ethylenediamine tetraacetic acid. Blood samples are mixed well and kept on ice until the completion of the experiment. Plasma will be obtained by centrifugation of the blood samples at 4° C. The plasma is separated and analyzed by gel filtration chromatography and the relative proportion of [$^3$H]CE in the VLDL, LDL and HDL regions will be determined.

The percentage [$^3$H]CE transferred from HDL to LDL and VLDL (% transfer) will be calculated based on the total radioactivity in equivalent plasma samples before precipitation. Typically, the amount of transfer from HDL to LDL and VLDL in control animals will be 20% to 35% after 30 min.

Intestinal Cholesterol Absorption Assay

A variety of compounds are shown to inhibit cholesterol absorption from the intestinal tract. These compounds lower serum cholesterol levels by reducing intestinal absorption of cholesterol from both exogenous sources (dietary cholesterol) and endogenous cholesterol (secreted by the gall bladder into the intestinal tract).

In hamsters the use of a dual-isotope plasma ratio method to measure intestinal cholesterol absorption has been refined and evaluated as described by Turley et al. (J. Lipid Res. 35, 329–339 (1994), herein incorporated by reference).

Male hamsters weighing 80–100 g are to be given food and water ad libitum in a room with 12 hour alternating periods of light and dark. Four hours into the light period, each hamster is administered first an intravenous dose of 2.5 μCi of [1,2-$^3$H]cholesterol suspended in Intralipid (20%) and then an oral dose of [4-$^{14}$C]cholesterol in an oil of medium chain triglycerides (MCT). The i.v. dose is given by injecting a 0.4 ml volume of the Intralipid mixture into the distal femoral vein. The oral dose is given by gavaging a 0.6 ml volume of the MCT oil mixture introduced intragastrically via a polyethylene tube. After 72 hours the hamsters are bled and the amount of $^3$H and $^{14}$C in the plasma and in the original amount of label administered are determined by liquid scintillation spectrometry. The cholesterol absorption will be calculated based on the following equation:

$$\text{Percent cholesterol absorbed} = \frac{\% \text{ of oral dose per ml of 72 hour plasma sample}}{\% \text{ of i.v. dose per ml of 72 hour plasma sample}} \times 100$$

Microsomal Triglyceride Transfer Protein (MTP) Assay

MTP can be purified from liver tissue or cultured cells (e.g. HepG2 cells) using standard methods as described by Ohringer et al. (Acta Crystallogr. D52, 224–225 (1996), herein incorporated by reference).

Subsequent analysis of MTP activity can be performed as described by Jamil et al. (Proc. Natl. Acad. Sci. 93, 11991–11995 (1996), herein incorporated by reference).

The basis of this assay is to measure the transfer of labeled triglycerides from a population of donor vesicles to a population of acceptor vesicles in the presence of MTP. Inhibitors of MTP can be evaluated by adding them to the mixture prior to the introduction of MTP. Donor vesicles are prepared by sonication of an aqueous mixture of egg phospholipids, cardiolipin, 3H-labeled phospholipid and $^{14}$C-labeled triglycerides. Acceptor vesicles are prepared by sonication of an aqueous mixture of egg phospholipids. The vesicle solutions are mixed together, with or without added MTP inhibitors, and MTP is added to initiate the transfer reaction. The assay is terminated after 60 minutes by addition of 0.5 ml of DE-52 cellulose followed by centrifugation to pellet the donor molecules. The amount of $^3$H and $^{14}$C in the pellet and in the original amount of label in the mixture are determined by liquid scintillation spectrometry. The lipid transfer rate will be calculated based on first order kinetics using the expression:

$$[S]=[S]_0 e^{-kt}$$

where $[S]_0$ and $[S]$ are the fractions of $^{14}$C label in the donor membrane pellet at times 0 and t, respectively, and the term k is the fraction of label transferred per unit time.

Plasma Lipids Assay in Rabbits

Plasma lipids can be assayed using standard methods as reported by J. R. Schuh et al., *J. Clin. Invest.*, 91, 1453–1458 (1993), herein incorporated by reference. Groups of male, New Zealand white rabbits are placed on a standard diet (100 g/day) supplemented with 0.3% cholesterol and 2% corn oil (Zeigler Bothers, Inc., Gardners, Pa.). Water is available ad lib. Groups of control and treated animals are killed after 1 and 3 months of treatment. Tissues are removed for characterization of atherosclerotic lesions. Blood samples are to be taken for determination of plasma lipid concentrations.

Plasma Lipids

Plasma for lipid analysis is to be obtained by withdrawing blood from the ear vein into EDTA-containing tubes (Vacutainer; Becton Dickenson & Co., Rutherford, N.J.), followed by centrifugal separation of the cells. Total cholesterol is determined enzymatically, using the cholesterol oxidase reaction (C. A. Allain et al., *Clin. Chem.*, 20, 470–475 (1974), herein incorporated by reference). HDL cholesterol is also measured enzymatically, after selective precipitation of LDL and VLDL by dextran sulfate with magnesium (G. R. Warnick et al., *Clin. Chem.*, 28, 1379–1388 (1982), herein incorporated by reference). Plasma triglyceride levels will be determined by measuring the amount of glycerol released by lipoprotein lipase through an enzyme-linked assay (G. Bucolo et al., *Clin. Chem.*, 19, 476–482 (1973), herein incorporated by reference).

Atherosclerosis

Animals are to be killed by pentobarbital injection. Thoracic aortas are rapidly removed, immersion fixed in 10% neutral buffered formalin, and stained with oil red O (0.3%). After a single longitudinal incision along the wall opposite the arterial ostia, the vessels are pinned open for evaluation of the plaque area. The percent plaque coverage is determined from the values for the total area examined and the stained area, by threshold analysis using a true color image analyzer (Videometric 150; American Innovision, Incl, San Diego, Calif.) interfaced to a color camera (Toshiba 3CCD) mounted on a dissecting microscope. Tissue cholesterol will be measured enzymatically as described, after extraction with a chloroform/methanol mixture (2:1) according to the method of Folch et al. (J. Biol. Chem., 226, 497–509 (1957), herein incorporated by reference).

In Vitro Vascular Response

The abdominal aortas are rapidly excised, after injection of sodium pentobarbital, and placed in oxygenated Krebs-bicarbonate buffer. After removal of perivascular tissue, 3-mm ring segments are cut, placed in a 37° C. muscle bath containing Krebs-bicarbonate solution, and suspended between two stainless steel wires, one of which is attached to a force transducer (Grass Instrument Co., Quincy, Mass.). Force changes in response to angiotensin II added to the bath will be recorded on a chart recorder.

The examples herein can be performed by substituting the generically or specifically described therapeutic compounds or inert ingredients for those used in the preceding examples.

The invention being thus described, it is apparent that the same can be varied in many ways. Such variations are not to be regarded as a departure from the spirit and scope of the present invention, and all such modifications and equivalents as would be obvious to one skilled in the art are intended to be included within the scope of the following claims.

What is claimed is:

1. A therapeutic combination comprising a first amount of a cholestery ester transfer protein inhibiting compound and a second amount of a bile acid sequestering compound wherein the first amount and the second amount together comprise an anti-hyperlipidemic condition effective amount, an anti-atherosclerotic condition effective amount, or an anti-hypercholesterolemic condition effective amount of the compounds, wherein said cholesteryl ester transfer protein inhibiting compound comprises compound C-12 represented by:

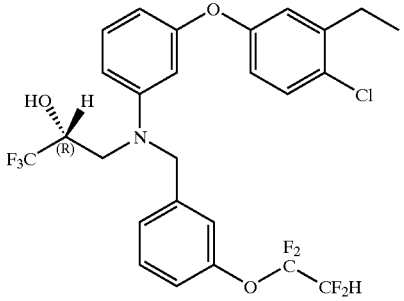

(C-12)

or enantiomers or racemates thereof.

2. The therapeutic combination of claim 1, wherein said bile acid sequestering compound comprises colesevelam hydrochloride.

3. The therapeutic combination of claim 1 wherein said bile acid sequestering compound comprises cholestyramine.

4. The therapeutic combination of claim 1 wherein said bile acid sequestering compound comprises colestipol.

5. The therapeutic combination of claim 1 wherein said bile acid sequestering compound comprises an amphiphilic copolymer having a crosslinked shell domain and an interior core domain.

6. The therapeutic combination of claim 1 wherein said bile acid sequestering compound comprises a polyallylamine polymer.

7. The therapeutic combination of claim 6 wherein said bile acid sequestering compound comprises colesevelam hydrochloride.

8. A method for the prophylaxis or treatment of a hyperlipidemic condition comprising administering, to a patient in need thereof, a combination in unit dosage form wherein the unit dosage form comprises a first amount of a cholesteryl ester transfer protein (CETP) inhibiting compound and a second amount of a bile acid sequestering (BAS) compound wherein the first amount and the second amount together comprises an anti-hyperlipidemic condition effective amount of said CETP inhibiting compound and said BAS compound, wherein said CETP inhibiting compound is represented by formula C-12:

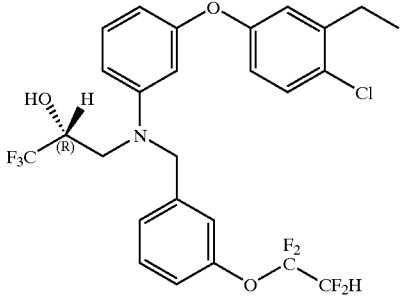

(C-12)

or enantiomers or racemates thereof.

9. A method for the prophylaxis or treatment of a hyperlipidemic condition comprising administering, to a patient in need thereof, a combination in unit dosage form wherein the unit dosage form comprises a first amount of a cholesteryl ester transfer protein (CETP) inhibiting compound and a second amount of a bile acid sequestering (BAS) compound wherein the first amount and the second amount together comprises an anti-atherosclerotic condition effective amount of said CETP inhibiting compound and said BAS compound, wherein said CETP inhibiting compound is represented by formula C-12:

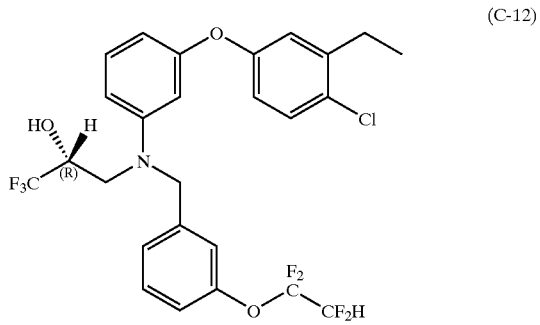

(C-12)

or enantiomers or racemates thereof.

10. A method for the prophylaxis or treatment of a hyperlipidemic condition comprising administering, to a patient in need thereof, a combination in unit dosage form wherein the unit dosage form comprises a first amount of a cholesteryl ester transfer protein (CETP) inhibiting compound and a second amount of a bile acid sequestering (BAS) compound wherein the first amount and the second amount together comprises an anti-hypercholesterolemic condition effective amount of said CETP inhibiting compound and said BAS compound, wherein said CETP inhibiting compound is represented by formula C-12:

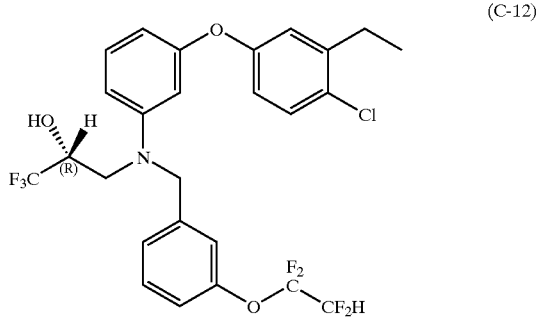

(C-12)

or enantiomers or racemates thereof.

* * * * *

UNITED STATES PATENT AND TRADEMARK OFFICE
CERTIFICATE OF CORRECTION

PATENT NO. : 6,569,905 B1
DATED : May 27, 2003
INVENTOR(S) : James A. Sikorski et al.

It is certified that error appears in the above-identified patent and that said Letters Patent is hereby corrected as shown below:

<u>Column 30,</u>
Line 61, "cholestery" has been replaced with -- cholesteryl --.

Signed and Sealed this

Second Day of March, 2004

JON W. DUDAS
*Acting Director of the United States Patent and Trademark Office*